(12) United States Patent
Chabrecek et al.

(10) Patent No.: US 6,878,399 B2
(45) Date of Patent: *Apr. 12, 2005

(54) METHOD FOR MODIFYING THE SURFACE OF BIOMEDICAL ARTICLES

(75) Inventors: Peter Chabrecek, Riehen (CH); Jörg Leukel, Freiburg (DE); Hynek Biedermann, Praha (CZ); Dieter Lohmann, Münchenstein (CH)

(73) Assignee: Novartis AG, Basel (CH)

( * ) Notice: Subject to any disclaimer, the term of this patent is extended or adjusted under 35 U.S.C. 154(b) by 42 days.

This patent is subject to a terminal disclaimer.

(21) Appl. No.: 10/292,836

(22) Filed: Nov. 12, 2002

(65) Prior Publication Data

US 2003/0219533 A1 Nov. 27, 2003

(30) Foreign Application Priority Data

Nov. 13, 2001 (EP) .............................. 01811088

(51) Int. Cl.⁷ .............................. B05D 5/06; A61L 2/00
(52) U.S. Cl. ...................... 427/162; 427/2.1; 427/2.24; 427/407.1
(58) Field of Search ........................ 427/162, 2.1, 2.24, 427/407.1

(56) References Cited

U.S. PATENT DOCUMENTS

| | | | |
|---|---|---|---|
| 4,588,624 A | 5/1986 | Nygren et al. | 428/36 |
| 4,929,685 A | 5/1990 | Kobashi et al. | 525/277 |
| 5,080,924 A | 1/1992 | Kamel et al. | 427/2 |
| 5,258,041 A | 11/1993 | Guire et al. | 623/66 |
| 5,527,925 A * | 6/1996 | Chabrecek et al. | 549/430 |
| 5,612,389 A | 3/1997 | Chabrecek et al. | 522/35 |
| 5,612,391 A | 3/1997 | Chabrecek et al. | 523/106 |
| 5,621,018 A | 4/1997 | Chabrecek et al. | 522/35 |
| 5,693,768 A | 12/1997 | Bachmann et al. | 536/4.1 |
| 6,087,412 A | 7/2000 | Chabrecek et al. | 522/35 |
| 6,099,122 A | 8/2000 | Chabrecek et al. | 351/160 |
| 6,169,127 B1 | 1/2001 | Lohmann et al. | 523/106 |
| 6,204,306 B1 | 3/2001 | Chabrecek et al. | 523/106 |
| 6,436,481 B1 | 8/2002 | Chabrecek et al. | 427/488 |
| 6,447,920 B1 * | 9/2002 | Chabrecek et al. | 428/423.1 |
| 6,451,871 B1 | 9/2002 | Winterton et al. | 523/106 |
| 6,465,056 B1 | 10/2002 | Chabrecek et al. | 427/557 |
| 6,468,667 B1 | 10/2002 | Chabrecek et al. | 428/532 |
| 6,521,358 B1 | 2/2003 | Tanaka et al. | 428/670 |
| 6,589,665 B2 * | 7/2003 | Chabrecek et al. | 428/520 |
| 2002/0086160 A1 | 7/2002 | Qiu et al. | 428/413 |
| 2003/0008063 A1 | 1/2003 | Chabrecek et al. | 427/2.1 |

FOREIGN PATENT DOCUMENTS

| | | |
|---|---|---|
| EP | 1 095 966 A2 | 5/2001 |
| WO | WO 96/20796 | 7/1996 |

OTHER PUBLICATIONS

International Search Report.

* cited by examiner

*Primary Examiner*—Elena Tsoy
(74) *Attorney, Agent, or Firm*—Jian Zhou; Robert Gorman; R. Scott Meece

(57) ABSTRACT

The invention relates to a process for coating a material surface, comprising the steps of:
(a) providing an inorganic or organic bulk material;
(b) providing one or more polyionic materials at least one of them comprising covalently bound initiator moieties for radical polymerization;
(c) applying the polyionic material of step (b) to the bulk material of step (a), thereby forming a hydrophilic layer on the bulk material surface; and
(d) graft polymerizing a hydrophilic monomer or macromonomer onto said polyionic material.

The coated articles that are obtainable by the process of the invention have desirable characteristics regarding adherence to the substrate, durability, hydrophilicity, wettability, biocompatibility and permeability and are thus useful for the manufacture of biomedical articles such as ophthalmic devices.

20 Claims, No Drawings

METHOD FOR MODIFYING THE SURFACE OF BIOMEDICAL ARTICLES

This application claims under 35 U.S.C. §119(a)–(d) or §365(b) of European Patent Application No. 01811088.2 filed Nov. 13, 2001.

The present invention relates to a method of modifying the surface of an inorganic or organic bulk material such as contact lenses and other biomedical articles by at least partially coating the surfaces of such materials with a hydrophilic polymer.

Many devices used in biomedical applications require that the bulk of the device have one property and the surface of the device have a different property. For example, contact lenses may require relatively high oxygen permeability through the bulk of the lens to maintain good corneal health. However, materials that exhibit exceptionally high oxygen permeability (e.g. polysiloxanes) are typically hydrophobic and, untreated or not surface modified, will adhere to the eye. Thus a contact lens will generally have a core bulk material that is highly oxygen permeable and hydrophobic, and a surface that has been treated or coated to increase hydrophilic properties. This hydrophilic surface allows the lens to move relatively freely on the eye without adhering excessive amounts of tear lipid and protein.

A variety of different types of processes for preparing hydrophilic polymeric coatings on an "inert" hydrophobic substrate have been disclosed in the prior art. For example, WO 99/57581 discloses to first of all provide the article surface with covalently bound photoinitiator molecules, coating the modified surface with a layer of a polymerizable macromonomer and then subjecting it to a heat or radiation treatment whereby the macromonomer is graft polymerized thus forming the novel article surface. The covalent binding of the photoinitiator molecules to the article surface is created by first subjecting the article surface to a plasma treatment thereby providing the surface with functional groups, and then reacting said functional groups with co-reactive groups of a functional photoinitiator.

A plasma treatment requires a considerable investment in equipment and is furthermore difficult to be integrated in an automated production process. For example, a plasma treatment requires that the article to be treated is dry before exposure to the plasma. Thus, a polymeric article such as a contact lens that is wet from prior hydration or extraction must be dried previously, thereby adding time in the overall lens production process as well as imposing added costs of obtaining a drying equipment.

Therefore, it would be highly desirable to modify the surface functionalization step of the process disclosed in WO 99/57581 such that the plasma treatment is avoided and replaced by a technique which is easy to perform with standard equipment and which is thus more feasible for an automated production process.

Surprisingly, it has now been found, that hydrophobic articles may be readily functionalized by applying at least one polyelectrolyte comprising covalently bound photoinitiator moieties for radical polymerization to the article surface followed by graft polymerization of suitable hydrophilic macromonomers onto the article surface.

The present invention therefore in one aspect relates to a process for coating a material surface comprising the steps of:
(a) providing an inorganic or organic bulk material;
(b) providing one or more polyionic materials at least one of them comprising covalently bound initiator moieties for radical polymerization;
(c) applying the polyionic material of step (b) to the bulk material of step (a), thereby forming a hydrophilic layer on the bulk material surface; and
(d) graft polymerizing a hydrophilic monomer or macromonomer onto said polyionic material.

Examples of suitable bulk materials are quartz, ceramics, glasses, silicate minerals, silica gels, metals, metal oxides, carbon materials such as graphite or glassy carbon, natural or synthetic organic polymers, or laminates, composites or blends of said materials, in particular natural or synthetic organic polymers or modified biopolymers which are known in large number. Some examples of polymers are polyaddition and polycondensation polymers (polyurethanes, epoxy resins, polyethers, polyesters, polyamides and polyimides); vinyl polymers (polyacrylates, polymethacrylates, polyacrylamides, polymethacrylamides, polystyrene, polyethylene and halogenated derivatives thereof, polyvinyl acetate and polyacrylonitrile); or elastomers (silicones, polybutadiene and polyisoprene).

A preferred group of materials to be coated are those being conventionally used for the manufacture of biomedical devices, e.g. contact lenses, in particular contact lenses for extended wear, which are not hydrophilic per se. Such materials are known to the skilled artisan and may comprise for example polysiloxanes, perfluoroalkyl polyethers, fluorinated poly(meth)acrylates or equivalent fluorinated polymers derived e.g. from other polymerizable carboxylic acids, polyalkyl(meth)acrylates or equivalent alkylester polymers derived from other polymerizable carboxylic acids, or fluorinated polyolefines, such as fluorinated ethylene or propylene, for example tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another group of preferred materials to be coated are amphiphilic segmented copolymers comprising at least one hydrophobic segment and at least one hydrophilic segment which are linked through a bond or a bridge member. Examples are silicone hydrogels, for example those disclosed in PCT applications WO 96/31792 and WO 97/49740.

A particular preferred group of bulk materials comprises organic polymers selected from polyacrylates, polymethacrylates, polyacrylamides, poly(N,N-dimethylacrylamides), polymethacrylamides, polyvinyl acetates, polysiloxanes, perfluoroalkyl polyethers, fluorinated polyacrylates or -methacrylates and amphiphilic segmented copolymers comprising at least one hydrophobic segment, for example a polysiloxane or perfluoroalkyl polyether segment or a mixed polysiloxane/perfluoroalkyl polyether segment, and at least one hydrophilic segment, for example a polyoxazoline, poly(2-hydroxyethylmethacrylate), polyacrylamide, poly(N,N-dimethylacrylamide), polyvinylpyrrolidone polyacrylic or polymethacrylic acid segment or a copolymeric mixture of two or more of the underlying monomers.

The material to be coated may also be any blood-contacting material conventionally used for the manufacture of renal dialysis membranes, blood storage bags, pacemaker leads or vascular grafts. For example, the material to be modified on its surface may be a polyurethane, polydimethylsiloxane, polytetrafluoroethylene, polyvinylchloride, Dacron™ or Silastic™ type polymer, or a composite made therefrom.

Moreover, the material to be coated may also be an inorganic or metallic base material without suitable reactive groups, e.g. ceramic, quartz, or metals, such as silicon or gold, or other polymeric or non-polymeric substrates. E.g. for implantable biomedical applications, ceramics are very useful. In addition, e.g. for biosensor purposes, hydrophilically coated base materials are expected to reduce nonspecific binding effects if the structure of the coating is well controlled. Biosensors may require a specific carbohydrate coating on gold, quartz, or other non-polymeric substrates.

The form of the material to be coated may vary within wide limits. Examples are particles, granules, capsules, fibres, tubes, films or membranes, preferably moldings of all kinds such as ophthalmic moldings, for example intraocular lenses, artificial cornea or in particular contact lenses.

Suitable substances that may be utilized to form the polymeric layer according to step (c) of the present invention include various polyionic materials which comprise reactive functional groups, to some of which initiator moieties for radical polymerization are covalently bound. The ratio of free reactive functional groups to functional groups bound to initiator moieties for radical polymerization may vary within wide limits, for example from 10:1 to 200:1.

A polymeric layer according to step (c) may comprise a single polymer, a first and a second ionic polymer having opposite charges or different polymers having the same or different charges. Said polymeric layer may also comprise polyionic materials, which are devoid of covalently bound initiator moieties for radical polymerization.

The polyionic materials to which initiator moieties for radical polymerization are covalently bound for use in step (b) include polyanionic and/or polycationic polymers. Examples of suitable anionic materials include, for example, a synthetic polymer, a biopolymer or modified polymer comprising carboxy, sulfo, sulfato, phosphono or phosphato groups or mixtures thereof, or a salt thereof, for example a biomedically acceptable salt and especially an ophthalmically acceptable salt thereof when the substrate to be coated is an ophthalmic device.

Examples of synthetic anionic materials are: a linear polyacrylic acid (PAA), a branched polyacrylic acid, for example a Carbophil or Carbopol type from Goodrich Corp., a polymethacrylic acid (PMA), a polyacrylic acid or polymethacrylic acid copolymer, for example a copolymer of acrylic or methacrylic acid and a further vinylmonomer, for example acrylamide, N,N-dimethyl acrylamide or N-vinylpyrrolidone, a maleic or fumaric acid copolymer, a poly(styrenesulfonic acid) (PSS), a polyamido acid, for example a carboxy-terminated polymer of a diamine and a di- or polycarboxylic acid, for example carboxy-terminated Starburst™ PAMAM dendrimers (Aldrich), a poly(2-acrylamido-2-methylpropanesulfonic acid) (poly-(AMPS)), or an alkylene polyphosphate, alkylene polyphosphonate, carbohydrate polyphosphate or carbohydrate polyphosphonate, for example a teichoic acid.

Examples of anionic biopolymers or modified biopolymers are: hyaluronic acid, glycosaminoglycanes such as heparin or chondroitin sulfate, fucoidan, polyaspartic acid, poly-glutamic acid, carboxymethyl cellulose, carboxymethyl dextranes, alginates, pectins, gellan, carboxyalkyl chitins, chitosan, carboxymethyl chitosans, sulphated polysaccharides.

A preferred anionic polymer is a linear or branched polyacrylic acid or an acrylic acid copolymer. A more preferred anionic polymer is a linear or branched polyacrylic acid. A branched polyarylic acid in this context is to be understood as meaning a polyacrylic acid obtainable by polymerizing acrylic acid in the presence of suitable (minor) amounts of a di- or polyvinyl compound.

A suitable cationic polymer is, for example, a synthetic polymer, biopolymer or modified biopolymer comprising primary or secondary amino groups or a suitable salt thereof, preferably an ophthalmically acceptable salt thereof, for example a hydrohalogenide such as a hydrochloride thereof.

Examples of synthetic cationic polymers are:
(i) a polyallylamine (PAH) homo- or copolymer, optionally comprising modifier units;
(ii) a polyethyleneimine (PEI);
(iii) a polyvinylamine homo- or copolymer, optionally comprising modifier units.
(iv) a poly(vinylbenzyl-tri-$C_1$–$C_4$-alkylammonium salt), for example a poly(vinylbenzyl-tri-methyl ammoniumchloride);
(v) a polymer of an aliphatic or araliphatic dihalide and an aliphatic N,N,N',N'-tetra-$C_1$–$C_4$-alkyl-alkylenediamine, for example a polymer of (a) propylene-1,3-dichloride or -dibromide or p-xylylene dichloride or dibromide and (b) N,N,N',N'-tetramethyl-1,4-tetramethylene diamine;
(vi) a poly(vinylpyridin) or poly(vinylpyridinium salt) homo- or copolymer;
(vii) a poly(N,N-diallyl-N,N-di-$C_1$–$C_4$-alkyl-ammoniumhalide) comprising units of formula

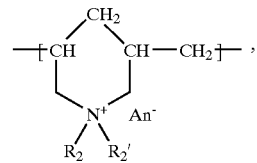

wherein $R_2$ and $R_2'$ are each independently $C_1$–$C_4$-alkyl, in particular methyl, and $An^-$ is a, for example, a halide anion such as the chloride anion;
(viii) a homo- or copolymer of a quaternized di-$C_1$–$C_4$-alkyl-aminoethyl acrylate or methacrylate, for example a poly(2-hydroxy-3-methacryloylpropyltri-$C_1$–$C_2$-alkylammonium salt) homopolymer such as a a poly(2-hydroxy-3-methacryloylpropyltri-methylammonium chloride), or a quaternized poly(2-dimethylaminoethyl methacrylate or a quaternized poly(vinylpyrrolidone-co-2-dimethylaminoethyl methacrylate);
(ix) POLYQUAD® as disclosed for example in EP-A-456,467; or
(x) a polyaminoamide (PAMAM), for example a linear PAMAM or a PAMAM dendrimer such as a amino-terminated Starbust™ PAMAM dendrimer (Aldrich).

Suitable modifier units of the polyallylamine (i) are known, for example from WO 00/31150.

The molecular weight of the anionic and cationic polymers used in step (b) may vary within wide limits depending on the desired characteristics such as adhesion on the bulk material, coating thickness and the like. In general, a weight average molecular weight of from about 5000 to about 5000000, preferably from 10000 to 1000000, more preferably from 15000 to 500000, even more preferably from 20000 to 200000 and in particular from 40000 to 150000, has proven as valuable both for anionic and cationic polymers used in step (b).

Examples of cationic biopolymers or modified biopolymers that may be used for the preparation of polyionic materials comprising covalently bound initiator moieties for radical polymerization according to step b) include: basic peptides, proteins or glucoproteins, for example, a poly-ε-lysine, albumin or collagen, aminoalkylated polysaccharides such as a chitosan or aminodextranes.

A preferred embodiment of an anionic material comprising covalently bound initiator moieties for radical polymerization is a derivative of a polyacrylic acid comprising structural units of formula $$* -[CH_2-CH]_g-[CH_2-CH]_h- * \quad (1)$$
$$\qquad | \qquad\qquad |$$
$$\qquad C=O \qquad C=O$$
$$\qquad | \qquad\qquad |$$
$$\qquad OH \qquad\qquad PI$$

wherein
PI is the radical of a photoinitiator,
the total of (g+h) is an integer from 15 to 10000; and
the ratio of g:h is from 200:1 to 10:1.

Preferred is a ratio of g:h is from 40:1 to 20:1.

Another preferred anionic materials for use in step b) are hyarulonic acid derivatives comprising structural units of formula (2)

wherein

PI is the radical of a photoinitiator,
the total of (g+h) is an integer from 15 to 25000; and
wherein the ratio of g:h is from 200:1 to 10:1.

Preferred is a ratio of g:h is from 40:1 to 10:1.

A preferred cationic material for use in step b) is a polyethyleneimine derivative comprising structural units of formula $$* -[CH_2-CH_2-NH]_g-[CH_2-CH_2-N]_h- *, \quad (3)$$
$$\qquad\qquad\qquad\qquad\qquad\qquad |$$
$$\qquad\qquad\qquad\qquad\qquad\qquad PI$$

wherein wherein $PI_1$ is the radical of a photoinitiator;
the total of (g+h) is an integer from 10 to 10000; and
wherein the ratio of g:h is from 200:1 to 1.0:1.

Preferred is a ratio of g:h is from 40:1 to 20:1.

Another preferred cationic material for use in step b) is a derivative of polyallylamine comprising structural units of formula $$* -[CH_2-CH]_g-[CH_2-CH]_h- * \quad (4)$$
$$\qquad | \qquad\qquad |$$
$$\qquad CH_2 \qquad\qquad CH_2$$
$$\qquad | \qquad\qquad |$$
$$\qquad NH_2 \qquad\qquad NH$$
$$\qquad\qquad\qquad\qquad |$$
$$\qquad\qquad\qquad\qquad PI$$

wherein $PI_1$ is the radical of a photoinitiator;
the total of (g+h) is an integer from 15 to 1000; and
the ratio of g:h is from 200:1 to 10:1.

Preferred is a ratio of g:h is from 40:1 to 20:1.

Functionalized photoinitiators suitable to be bound to reactive functional groups of polyionic materials are known and are described in, for example, WO 86/05778, EP 0 632 329 B1 and EP 800 511 B1.

Suitable photoinitiator radicals PI for polyionic materials of formula (3) and (4) are, for example, photoinitiator radicals $PI_1$ of formula (5a)

(5b)

(5c)

for polyionic materials of formula (1) and (2) photoinitiator radicals $PI_2$ of formula

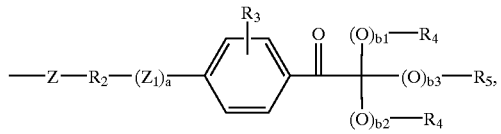 (5d)

wherein Z is bivalent —O—, —NH— or —NR$_{12}$—; Z$_1$ is —O—, —O—(O)C—, —C(O)—O— or —O—C(O)—O—; R$_3$ is H, C$_1$–C$_{12}$-alkyl, C$_1$–C$_{12}$-alkoxy or N—C$_1$–C$_{12}$-alkylamino; R$_4$ and R$_5$ are each independently of the other H, linear or branched C$_1$–C$_8$-alkyl, C$_1$–C$_8$-hydroxyalkyl or C$_6$–C$_{10}$-aryl, or the groups R$_4$—(O)$_{b1}$— and R$_4$—(O)$_{b2}$— together are —(CH$_2$)$_c$— wherein c is an integer from 3 to 5, or the groups R$_4$—(O)$_{b1}$—, R$_4$—(O)$_{b2}$— and R$_5$—(O$_1$)$_{b3}$— together are a radical of the formula

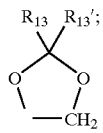

R$_2$ is a direct bond or linear or branched C$_1$–C$_8$-alkylene that is unsubstituted or substituted by —OH and/or is uninterrupted or interrupted by one or more groups —O—, —O—C(O)— or —O—C(O)—O—; R$_1$ is branched C$_3$–C$_{18}$-alkylene, unsubstituted or C$_1$–C$_4$-alkyl- or C$_1$–C$_4$-alkoxy-substituted C$_6$–C$_{10}$-arylene, or unsubstituted or C$_1$–C$_4$-alkyl- or C$_1$–C$_4$-alkoxy-substituted C$_7$–C$_{18}$-aralkylene, unsubstituted or C$_1$–C$_4$-alkyl- or C$_1$–C$_4$-alkoxy-substituted C$_3$–C$_8$-cycloalkylene, unsubstituted or C$_1$–C$_4$-alkyl- or C$_1$–C$_4$-alkoxy-substituted C$_3$–C$_8$-cycloalkylene-C$_y$H$_{2y}$— or unsubstituted or C$_1$–C$_4$-alkyl- or C$_1$–C$_4$-alkoxy-substituted —C$_y$H$_{2y}$—(C$_3$–C$_8$-cycloalkylene)-C$_y$H$_{2y}$— wherein y is an integer from 1 to 6; R$_6$ independently has the same definitions as R$_1$ or is linear C$_3$–C$_{18}$-alkylene; R$_{12}$ is linear or branched C$_1$–C$_6$-alkyl which may be further substituted, for example by hydroxy; T is bivalent —O—, —NH—, —S—, C$_1$–C$_8$-alkylene or

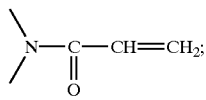

Z$_2$ is a direct bond or —O—(CH$_2$)$_d$— or —(OCH$_2$CH$_2$)$_d$— wherein d is an integer from 1 to 6 and the terminal CH$_2$ group of which is each linked to the adjacent T in formula (3c); R$_8$ is linear or branched C$_1$–C$_8$-alkyl, C$_2$–C$_8$-alkenyl or C$_6$–C$_{10}$-aryl-C$_1$–C$_8$-alkyl; R$_9$ independently of R$_8$ has the same definitions as R$_8$ or is C$_6$–C$_{10}$-aryl, or R$_8$ and R$_9$ together are —(CH$_2$)$_e$— wherein e is an integer from 2 to 6; R$_{10}$ and R$_{11}$ are each independently of the other linear or branched C$_1$–C$_8$-alkyl that may be substituted by C$_1$–C$_4$-alkoxy, or C$_6$–C$_{10}$-aryl-C$_1$–C$_8$-alkyl or C$_2$–C$_8$-alkenyl; or R$_{10}$ and R$_{11}$ together are —(CH$_2$)$_{f1}$—Z$_3$—(CH$_2$)$_{f2}$— wherein Z$_3$ is a direct bond, —O—, —S— or —NR$_7$—, and R$_7$ is H or C$_1$–C$_8$-alkyl and f1 and f2 are each independently of the other an integer from 2 to 4; R$_{13}$ and R$_{13}$' are each independently of the other H, C$_1$–C$_8$-alkyl, C$_3$–C$_8$-cycloalkyl, benzyl or phenyl; and a, a1, b1, b2 and b3 are each independently of the other 0 or 1; subject to the provisos that b1 and b2 are each 0 when R$_{15}$ is H; that the total of (b1+b2+b3) is not exceeding 2; and that a is 0 when R$_{12}$ is a direct bond.

Some examples of photoinitiators especially preferred for the covalent attachment to the polyionic material are isocyanate bearing compounds of formula

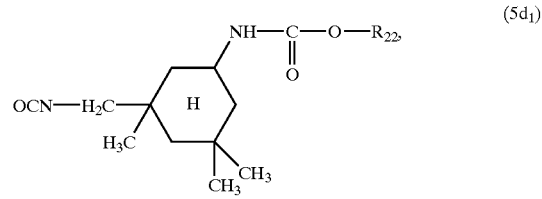 (5d$_1$)

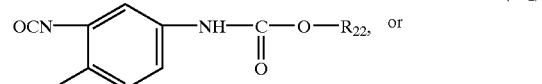 (5d$_2$)

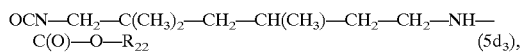 (5d$_3$), wherein R$_{22}$ is a radical

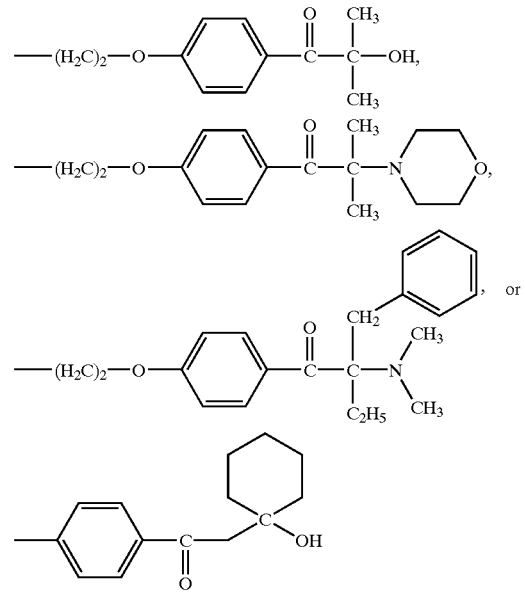

The photoinitiator groups of the polyionic materials of step b) are covalently bound to reactive functional groups of the requisite polymer by using a photoinitiator with a co-reactive functional group.

The covalent coupling of the functional groups of the polyionic material with co-reactive groups of a photoinitiator are well-known in the art and may be carried out as described in textbooks of organic chemistry.

For example, the reaction of amino or hydroxy groups of a polyionic material with isocyanato or isothiocyanato groups of a photoinitiator, may be carried out in an organic solvent such as, for example petroleum ether, methylcyclohexane, toluene, acetonitrile, chloroform, methylene chloride and the like, or an ether, for example diethyl ether, tetrahydrofurane, dioxane, or a more polar solvent such as DMSO, DMA, N-methylpyrrolidone, at a temperature of from 0 to 100° C., preferably from 0 to 50° C. and particularly preferably at room temperature, optionally in the presence of a catalyst, for example a tertiary amine such as triethylamine or tri-n-butylamine, 1,4- diazabicyclooctane, or a tin compound such as dibutyltin dilaurate or tin dioctanoate. It is advantageous to carry out the above reactions under an inert atmosphere, for example under a nitrogen or argon atmosphere.

In case that the polyionic material comprises a carboxy group, the reaction of the carboxy group with an amino or hydroxy group of a functionalized photoinitiator, or vice versa the reaction of an amino or hydroxy group of the polyionic material with a carboxy functionalized polymerisation initiator, may be carried out under the conditions that are customary for ester or amide formation, for example in an polar solvent at a temperature from about room temperature to about 100° C. It is further preferred to carry out the esterification or amidation reaction in the presence of an activating agent, for example N-ethyl-N'-(3-dimethylaminopropyl)carbodiimide (EDC), N-hydroxy succinimide (NHS), sulfo-N-hydroxy succinimide or N,N'-dicyclohexyl carbodiimide (DCC) or in the presence of an o-(benztriazole)-uronium salt such as o-(benztriazol-1-y-)-N,N,N,N-tetramethyluronium hexafluorophosphate. Most preferably, the carboxy group $L_2$ is previously converted to an activated ester using one of the above-mentioned activating agents, and the activated ester is then further reacted with the hydroxy or preferably amino groups.

The application of the polyionic materials according to step (b) may be accomplished according to processes known per se. For example, the bulk material is immersed in a solution of the anionic and cationic polymer, or one or more layers each of the anionic and cationic polymer are successively deposited on the modified bulk material surface, for example by dipping, spraying, printing, spreading, pouring, rolling, spin coating or vacuum vapor deposition, spraying or particularly dipping being preferred. Following the deposition of one ionic polymer the bulk material may be rinsed or dried before the deposition of the next ionic polymer having opposite charges. However, it is preferred to omit a rinsing or drying step between the attachment of the first and second ionic polymer.

A preferred dip method involves the steps of (i) applying a coating of a first ionic polymer, for example of a cationic or preferably of an anionic polymer, to the bulk material by immersing the bulk material in a solution of the first ionic polymer; (ii) optionally, rinsing the bulk material by immersing it in a rinsing solution; (iii) optionally, drying said bulk material; and (iv) applying a coating of a second ionic polymer having charges opposite of the charges of the first ionic polymer, for example an anionic or preferably a cationic polymer, to the bulk material by immersing the bulk material in a solution of the second ionic polymer. A more preferred dip method involves the steps of applying a coating of the first and second ionic polymer by immersing the bulk material successively in a solution each of the first and second ionic polymer without a rinsing or drying step in between. A further dip method involves immersing the bulk material in a solution comprising both the anionic and cationic polymer.

In the above-mentioned processes, at least one of the ionic polymers, for example the cationic or the anionic, or both, comprise a covalently bound photoinitiator.

The dip solutions of the anionic and cationic polymer in general comprise the respective polymer diluted in one or more different solvents. Suitable solvents are, for example, water or an aqueous solution comprising a water-miscible organic solvent, for example a $C_1$–$C_4$-alkanol such as methanol or ethanol; the preferred solvent is pure water. The aqueous solutions of the cationic or anionic polymer advantageously each have a slightly acidic pH value, for example a pH from about 2 to about 5 and preferably from about 2.5 to about 4.5. The concentration of the dip solutions may vary within wide limits depending, for example, on the particular ionic polymer involved. However, it is generally preferred to formulate relatively dilute solutions of the ionic polymers. A preferred anionic or cationic polymer concentration is from about 0.0001 to about 0.25 weight percent, more preferably from 0.0005 to 0.15 weight percent and in particular from 0.001 to 0.1 percent by weight, relative to the total weight of the solution.

A suitable rinsing solution, if used, is preferably an aqueous solution, in particular an aqueous solution buffered at a pH of about 2 to about 7, more preferably from 2 to 5 and even more preferably from 2.5 to 4.5.

Partial drying or removal of excess rinsing solution from the surface between solution applications, if applicable, may be accomplished by a number of means known in the art. While the bulk material may be partially dried by merely allowing the lens to remain in an air atmosphere for a certain period of time, it is preferable to accelerate the drying by application of a mild stream of air to the surface. The flow rate may be adjusted as a function of the strength of the material being dried and the mechanical fixturing of the material. It should be noted that there is no requirement to completely dry the bulk material. The "partial drying" step, as used herein, refers to a removal of droplets of solution which cling to the lens surface, rather than a desiccation of the lens. Thus, it is preferred to dry only to the extent that any water or solution film on the surface is removed.

Hydrophilic ethylenically unsaturated macromonomers for graft polymerization from the bulk material surface according to step (d) of the process of the present invention are known, for example, from WO 99/57581. A suitable macromonomer is, for example of formula

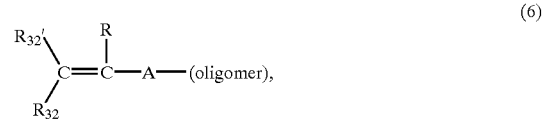

(6)

wherein $R_{32}$ is hydrogen, $C_1$–$C_6$-alkyl or a radical —COOR';

R, R' and $R_{32}'$ are each independently of the other hydrogen or $C_1$–$C_6$-alkyl;

A is a direct bond or is a radical of formula

(7a) or

(7b); or

(7c); or

(7d); or

(7e); or

A and $R_{32}$, together with the adjacent double bond, are a radical of formula

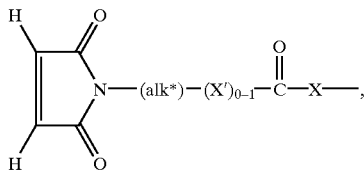

(7f)

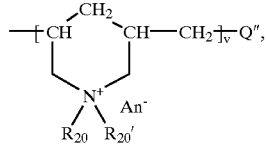

(8c)

$A_1$ is —O—$C_2$–$C_{12}$-alkylene which is unsubstituted or substituted by hydroxy, or is —O—$C_2$–$C_{12}$-alkylene-NH—C(O)— or —O—$C_2$–$C_{12}$-alkylene-O—C(O)—NH—$R_{33}$—NH—C(O)— or —NH-(Alk*)-C(O)—, wherein (Alk*) is $C_1$–$C_6$-alkylene and $R_{33}$ is linear or branched $C_1$–$C_{18}$-alkylene or unsubstituted or $C_1$–$C_4$-alkyl- or $C_1$–$C_4$-alkoxy-substituted $C_6$–$C_{10}$-arylene, $C_7$–$C_{18}$-aralkylene, $C_6$–$C_{10}$-arylene-$C_1$–$C_2$-alkylene-$C_6$–$C_{10}$-arylene, $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene;

$A_2$ is $C_1$–$C_8$-alkylene; phenylene or benzylene;

m and n are each independently of the other the number 0 or 1;

X, $X_1$ and X' are each independently of the other a bivalent group —O— or —NR", wherein R" is hydrogen or $C_1$–$C_6$-alkyl;

(alk*) is $C_2$–$C_{12}$-alkylene;

and (oligomer) denotes (i) the radical of a telomer of formula

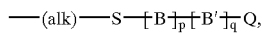

(8a)

wherein (alk) is $C_2$–$C_{12}$-alkylene,

Q is a monovalent group that is suitable to act as a polymerization chain-reaction terminator, p and q are each independently of another an integer from 0 to 350, wherein the total of (p+q) is an integer from 2 to 350, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (ii) the radical of an oligomer of the formula

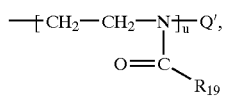

(8b)

wherein $R_{19}$ is hydrogen or unsubstituted or hydroxy-substituted $C_1$–$C_{12}$-alkyl, u is an integer from 2 to 250 and Q' is a radical of a polymerization initiator; or (iii) the radical of formula

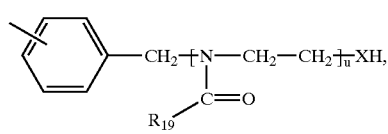

(8b')

wherein $R_{19}$, X and u are as defined above, or (iv) the radical of an oligomer of formula wherein $R_{20}$ and $R_{20}'$ are each independently $C_1$–$C_4$-alkyl, An⁻ is an anion, v is an integer from 2 to 250, and Q" is a monovalent group that is suitable to act as a polymerization chain-reaction terminator; or (v) the radical of an oligopeptide of formula

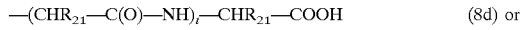 (8d) or

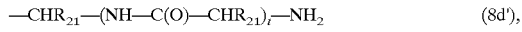 (8d'), wherein $R_{21}$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—$NH_2$ and t is an integer from 2 to 250, or the radical of an oligopeptide based on proline or hydroxyproline; or (vi) the radical of a polyalkylene oxide of formula

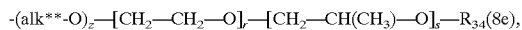(8e), wherein $R_{34}$ is hydrogen or $C_1$–$C_{24}$-alkyl, (alk**) is $C_2$–$C_4$-alkylene, z is 0 or 1, r and s are each independently an integer from 0 to 250 and the total of (r+s) is from 2 to 250; or (vii) the radical of an oligosaccharide;

subject to the provisos that

A is not a direct bond if (oligomer) is a radical of formula (8a);

A is a radical of formula (7a), (7b) or (7d) or A and $R_{32}$, together with the adjacent double bond, are a radical of formula (7f) if (oligomer) is a radical of formula (8b), (8c), (8d) or (8e) or is the radical of an oligosaccharide;

A is a direct bond if (oligomer) is a radical of formula (8b'); and

A is a radical of formula (7c) or (7e) if (oligomer) is a radical of formula (8d').

The following preferences apply to the variables contained in the definition of the macromonomer of formula (6):

R' is preferably hydrogen or $C_1$–$C_4$-alkyl, more preferably hydrogen or $C_1$–$C_2$-alkyl and particularly preferably hydrogen.

$R_{32}$ is preferably hydrogen, methyl or carboxyl, and particularly preferably hydrogen.

R is preferably hydrogen or methyl.

X is preferably a bivalent group —O— or —NH—. X is particularly preferably the group —NH— if (oligomer) is a radical of formula (8a); (8c) or (8d), and is particularly preferably the group —O— if (oligomer) is a radical of formula (8b) or (8e) or is the radical of an oligosaccharide. X' is preferably —O— or —NH— and more preferably —NH—. $X_1$ is preferably —O— or —NH—.

The radical $R_{33}$ has a symmetrical or, preferably, an asymmetrical structure. $R_{33}$ is preferably linear or branched $C_6$–$C_{10}$ alkylene; cyclohexylene-methylene or cyclohexylene-methylene-cyclohexylene each unsubstituted or substituted in the cyclohexyl moiety by from 1 to 3 methyl groups; or phenylene or phenylene-methylene-phenylene each unsubstituted or substituted in the phenyl moiety by methyl. The bivalent radical $R_{33}$ is derived preferably from a diisocyanate and most preferably from a diisocyanate selected from the group isophorone diisocyanate (IPDI), toluylene-2,4-diisocyanate (TDI), 4,4'-methylenebis(cyclohexyl isocyanate), 1,6-diisocyanato-2,2,4-trimethyl-n-hexane (TMDI), methylenebis(phenyl isocyanate), methylenebis(cyclohexyl-4-isocyanate) and hexamethylene diisocyanate (HMDI).

Preferred meanings of $A_1$ are unsubstituted or hydroxy-substituted —O—$C_2$–$C_8$-alkylene or a radical —O—$C_2$–$C_6$-alkylene-NH—C(O)— and particularly —O—$(CH_2)_{2-4}$—, —O—$CH_2$—CH(OH)—$CH_2$— or a radical —O—$(CH_2)_{2-4}$—NH—C(O)—. A particularly preferred meaning of $A_1$ is the radical —O—$(CH_2)_2$—NH—C(O)—.

$A_2$ is preferably $C_1$–$C_6$-alkylene, phenylene or benzylene, more preferably $C_1$–$C_4$-alkylene and even more preferably $C_1$–$C_2$-alkylene.

n is an integer of 0 or preferably 1, m is preferably an integer of 1.

$R_{32}'$ is preferably hydrogen or methyl and particularly preferably hydrogen.

In case that (oligomer) is a radical of formula (8a), (8b), (8c), (8d) or (8e) or is the radical of an oligosaccharide, is A preferably a radical of formula (7a) or (7b) and particularly preferably a radical of formula (7a), wherein the above given meanings and preferences apply for the variables contained therein.

A preferred group of hydrophilic macromonomers according to the invention comprises compounds of the above formula (6), wherein R is hydrogen or methyl, $R_{32}$ is hydrogen, methyl or carboxyl, $R_{32}'$ is hydrogen, A is a radical of the formula (7a) or (7b) and (oligomer) is a radical of formula (6a), (8b), (8c), (8d) or (8e) or is the radical of an oligosaccharide. An even more preferred group of hydrophilic macromonomers comprises compounds of the above formula (4), wherein R is hydrogen or methyl, $R_{32}$ and $R_{32}'$ are each hydrogen, A is a radical of the formula (7a) and (oligomer) is a radical of formula (8a). A further group of preferred macromonomers comprises compounds of formula (6), wherein A is a radical of formula (7e) above and (oligomer) is a radical of formula (8a).

(Alk*) is preferably methylene, ethylene or 1,1-dimethyl-methylene, in particular a radical —$CH_2$— or —C$(CH_3)_2$—.

(alk) and (alk*) are each independently preferably $C_2$–$C_8$-alkylene, more preferably $C_2$–$C_6$-alkylene, even more preferably $C_2$–$C_4$-alkylene and particularly preferably 1,2-ethylene. The alkylene radicals (alk) and (alk*) may be branched or preferably linear alkylene radicals.

Q is for example hydrogen.

The total of (p+q) is preferably an integer from 2 to 150, more preferably from 5 to 100, even more preferably from 5 to 75 and particularly preferably from 10 to 50. In a preferred embodiment of the invention q is 0 and p is an integer from 2 to 250, preferably from 2 to 150, more preferably from 5 to 100, even more preferably from 5 to 75 and particularly preferably from 10 to 50.

Suitable hydrophilic substituents of the radicals B or B' are those described in WO 99/57581 on pages 16 to 24.

A group of preferred non-ionic substituents of B or B' comprises $C_1$–$C_2$-alkyl, which is unsubstituted or substituted by —OH or —$NR_{23}R_{23}'$, wherein $R_{23}$ and $R_{23}'$ are each independently of the other hydrogen or $C_1$–$C_2$-alkyl; a radical —COOY wherein Y is $C_1$–$C_4$-alkyl; $C_2$–$C_4$-alkyl which is substituted by —OH, —$NR_{23}R_{23}'$ wherein $R_{23}$ and $R_{23}'$ are each independently of another hydrogen or $C_1$–$C_2$-alkyl, or Y is a radical —$C_2$–$C_4$-alkylene-NH—C(O)—O-G wherein —O-G is the radical of a saccharide; a radical —C(O)—$NY_1Y_2$, wherein $Y_1$ and $Y_2$ are each independently of the other hydrogen or $C_1$–$C_6$-alkyl which is unsubstituted or substituted by hydroxy, or $Y_1$ and $Y_2$ together with the adjacent N-atom form a heterocyclic 6-membered ring having no further heteroatom or having one further N- or O-atom; a radical —$OY_3$, wherein $Y_3$ is hydrogen, $C_1$–$C_4$-alkyl which is unsubstituted or substituted by —$NH_2$ or —N$(C_1$–$C_2$-alkyl)$_2$, or is a group —C(O)$C_1$–$C_2$-alkyl; or a 5- or 6-membered heteroaromatic or heteroaliphatic radical having one N-atom and in addition no further heteroatom or an additional N-, O- or S-heteroatom, or a 5 to 7-membered lactame.

A group of more preferred non-ionic substituents of B or B' comprises a radical —COOY, wherein Y is $C_1$–$C_2$-alkyl, $C_2$–$C_3$-alkyl, which is substituted by hydroxy, amino or N,N-di-$C_1$–$C_2$-alkylamino, or is a radical —$C_2$–$C_4$-alkylene-NH—C(O)—O-G wherein —O-G is the radical of trehalose; a radical —CO—$NY_1Y_2$, wherein $Y_1$ and $Y_2$ are each independently of the other hydrogen or $C_1$–$C_4$-alkyl which is unsubstituted or substituted by hydroxy, or $Y_1$ and $Y_2$ together with the adjacent N-atom form a N—$C_1$–$C_2$-alkylpiperazino or morpholino ring; or a heterocyclic radical selected from the group consisting of N-pyrrolidonyl, 2- or 4-pyridinyl, 2-methylpyridin-5-yl, 2-, 3-oder 4-hydroxypyridinyl, N-ε-caprolactamyl, N-imidazolyl, 2-methylimidazol-1-yl, N-morpholinyl and 4-N-methylpiperazin-1-yl.

A particularly preferred group of non-ionic substituents of B or B' comprises the radicals —$CONH_2$, —CON$(CH_3)_2$,

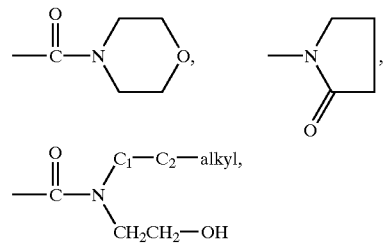

—CONH—$(CH_2)_2$—OH, —COO—$(CH_2)_2$—N$(CH_3)_2$, and —COO$(CH_2)_{2-4}$—NHC(O)—O-G wherein —O-G is the radical of trehalose.

Particularly preferred anionic substituents of B or B' are —COOH, —$SO_3H$, o-, m- or p-sulfophenyl, o-, m- or p-sulfomethylphenyl or a radical —$CONY_5Y_6$ wherein $Y_5$ is $C_2$–$C_4$-alkyl substituted by sulfo, and $Y_6$ is hydrogen.

A preferred cationic substituent of B or B' is a radical —C(O)$OY_7$ wherein $Y_7$ is $C_2$–$C_4$-alkyl, which is substituted by —N$(C_1$–$C_2$-alkyl)$_3^+$An$^-$ and is further substituted by hydroxy, and An$^-$ is an anion, for example the radical —C(O)O—$CH_2$—CH(OH)—$CH_2$—N$(CH_3)_3^+$An$^-$.

A preferred group of zwitter-ionic substituents —$R_{24}$-Zw corresponds to the formula

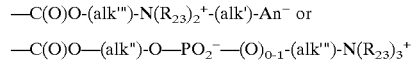

wherein $R_{23}$ is hydrogen or $C_1$–$C_6$-alkyl; An$^-$ is an anionic group —COO$^-$, —$SO_3^-$, —$OSO_3^-$ or —$OPO_3H^-$, preferably —COO$^-$ or —$SO_3^-$ and most preferably —$SO_3^-$, alk' is $C_1$–$C_{12}$-alkylene, (alk'') is $C_2$–$C_{24}$-alkylene which is unsubstituted or substituted by a radical —$OY_8$, $Y_8$ is hydrogen or the acyl radical of a carboxylic acid, and (alk''') is $C_2$–$C_8$-alkylene.

(alk') is preferably $C_2$–$C_8$-alkylene, more preferably $C_2$–$C_6$-alkylene and most preferably $C_2$–$C_4$-alkylene.

(alk**) is preferably $C_2$–$C_{12}$-alkylene, more preferably $C_2$–$C_6$-alkylene and particularly preferably $C_2$–$C_3$-alkylene which is in each case unsubstituted or substituted by hydroxy or by a radical —$OY_8$. (alk''') is preferably $C_2$–$C_4$-alkylene and more preferably $C_2$–$C_3$-alkylene. $R_{23}$ is hydrogen or $C_1$–$C_4$-alkyl, more preferably methyl or ethyl and particularly preferably methyl. A preferred zwitterionic substituent of B or B' is of formula

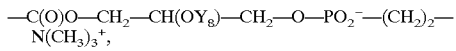

wherein $Y_8$ is hydrogen or the acyl radical of a higher fatty acid.

B denotes for example a radical of formula

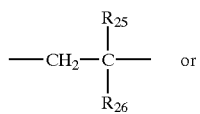  (9a)

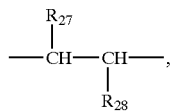  (9b)

wherein $R_{25}$ is hydrogen or $C_1$–$C_4$-alkyl, preferably hydrogen or methyl; $R_{26}$ is a hydrophilic substituent, wherein the above given meanings and preferences apply; $R_{27}$ is $C_1$–$C_4$-alkyl, phenyl or a radical —$C(O)OY_9$, wherein $Y_9$ is hydrogen or unsubstituted or hydroxy-substituted $C_1$–$C_4$-alkyl; and $R_{28}$ is a radical —$C(O)Y_9'$ or —$CH_2$—$C(O)OY_9'$ wherein $Y_9'$ independently has the meaning of $Y_9$.

$R_{27}$ is preferably $C_1$–$C_2$-alkyl, phenyl or a group —$C(O)OY_9$. $R_{28}$ is preferably a group —$C(O)OY_9'$ or —$CH_2$—$C(O)OY_9'$ wherein $Y_9$ and $Y_9'$ are each independently of the other hydrogen, $C_1$–$C_2$-alkyl or hydroxy-$C_1$–$C_2$-alkyl. Particularly preferred —$CHR_{27}$—$CHR_{28}$— units according to the invention are those wherein $R_{27}$ is methyl or a group —$C(O)OY_9$ and $R_{28}$ is a group —$C(O)OY_9'$ or —$CH_2$—$C(O)OY_9'$ wherein $Y_9$ and $Y_9'$ are each hydrogen, $C_1$–$C_2$-alkyl or hydroxy-$C_1$–$C_2$-alkyl.

B' independently may have one of the meanings given above for B.

If (oligomer) is a radical of formula (6a), the radical -(alk)-S—$[B]_p$—$[B']_q$-Q preferably denotes a radical of formula

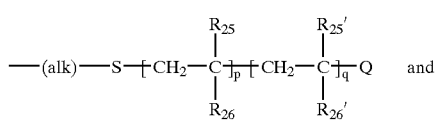  (8a')

and even more preferably of the formula

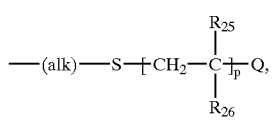  (8a'')

wherein for $R_{25}$, $R_{26}$, Q, p and q the above-given meanings and preferences apply, for $R_{25}'$ independently the meanings and preferences given before for $R_{25}$ apply, and for $R_{26}'$ independently the meanings and preferences given before for $R_{26}$ apply.

A preferred group of suitable hydrophilic macromonomers for use in step (d) of the invention comprises compounds of formula

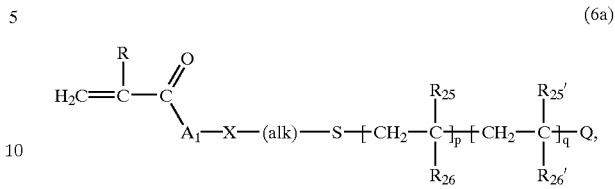  (6a)

wherein R is hydrogen or methyl, $A_1$ is —O—$(CH_2)_{2-4}$—, —O—$CH_2$—$CH(OH)$—$CH_2$— or a radical —O—$(CH_2)_{2-4}$—NH—$C(O)$—, X is —O— or —NH—, (alk) is $C_2$–$C_4$-alkylene, Q is a monovalent group that is suitable to act as a polymerization chain-reaction terminator, p is an integer from 5 to 50, $R_{25}$ and $R_{25}'$ are each independently of the other hydrogen or methyl, and for $R_{26}$ and $R_{26}'$ each independently the above given meanings and preferences apply.

A particularly preferred embodiment of the invention relates to hydrophilic macromonomers of the formula

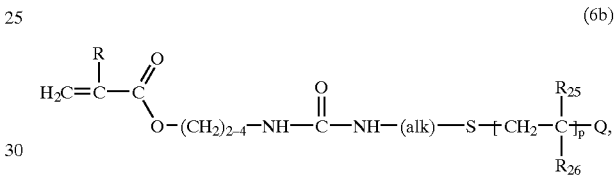  (6b)

wherein for R, $R_{25}$, $R_{26}$, Q, (alk) and p the above-given meanings and preferences apply. A particularly preferred group of hydrophilic macromonomers are compounds of the above formula (4b) wherein R is hydrogen or methyl, (alk) is $C_2$–$C_4$-alkylene, $R_{25}$ is hydrogen or methyl, p is an integer of 5 to 50, Q is as defined before, and for $R_{26}$ the above given meanings and preferences apply; in particular $R_{26}$ of this embodiment is a radical —$CONH_2$, —$CON(CH_3)_2$ or

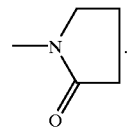

If (oligomer) is a radical (ii) of formula (6b), Q' in formula (6b) is for example $C_1$–$C_{12}$-alkyl, phenyl or benzyl, preferably $C_1$–$C_2$-alkyl or benzyl and in particular methyl. $R_{19}$ is preferably unsubstituted or hydroxy-substituted $C_1$–$C_4$-alkyl and in particular methyl, u is preferably an integer from 2 to 150, more preferably from 5 to 100, even more preferably from 5 to 75 and particularly preferably from 10 to 50.

If (oligomer) is a radical of formula (8b'), the above given meanings and preferences apply for the variables $R_{19}$ and u contained therein. X in formula (8b') is preferably hydroxy or amino.

If (oligomer) denotes a radical (iv) of formula (6c), $R_{20}$ and $R_{20}'$ are each preferably ethyl or in particular methyl; v is preferably an integer from 2 to 150, more preferably from 5 to 100, even more preferably from 5 to 75 and particularly preferably from 10 to 50; Q'' is for example hydrogen; and $An^-$ is as defined before.

If (oligomer) denotes an oligopeptide radical (v) of formula (8d) or 8d'), $R_{21}$ is for example hydrogen, methyl, hydroxymethyl, carboxymethyl, 1-hydroxyethyl, 2-carboxyethyl, isopropyl, n-, sec. or iso-butyl, 4-amino-n-butyl, benzyl, p-hydroxybenzyl, imidazolylmethyl, indolylmethyl or a radical —$(CH_2)_3$—NH—C(=NH)—$NH_2$, t is preferably an integer from 2 to 150, more preferably from 5 to 100, even more preferably from 5 to 75 and particularly preferably from 10 to 50.

If (oligomer) denotes a polyoxyalkylene radical (vi) of formula (8e), $R_{34}$ is preferably hydrogen or $C_1$–$C_{18}$-alkyl, more preferably hydrogen or $C_1$–$C_{12}$-alkyl, even more preferably hydrogen, methyl or ethyl, and particularly preferably hydrogen or methyl, (alk") is preferably a $C_2$–$C_3$-alkylene radical, z is preferably 0, r and s are each independently preferably an integer from 0 to 100 wherein the total of (r+s) is 5 to 100, r and s are each independently more preferably an integer from 0 to 50 wherein the total of (r+s) is 8 to 50. In a particularly preferred embodiment of the polyoxyalkylene radicals (oligomer), r is an integer from 8 to 50 and particularly 9 to 25, and s is 0.

(oligomer) as the radical of an oligosaccharide (vii) may be, for example, a di- or polysaccharide including carbohydrate containing fragments from a biopolymer. Examples are the radical of a cyclodextrin, trehalose, cellobiose, maltotriose, maltohexaose, chitohexaose or a starch, hyaluronic acid, deacetylated hyaluronic acid, chitosan, agarose, chitin 50, amylose, glucan, heparin, xylan, pectin, galactan, glycosaminoglycan, mucin, dextran, aminated dextran, cellulose, hydroxyalkylcellulose or carboxyalkylcellulose oligomer, each of which with a molecular weight average weight of, for example, up to 25,000 Da, preferably up to 10,000 Da. Preferably the oligosaccharide according to (vii) is the radical of a cyclodextrin with a maximum of 8 sugar units.

Formulae (8a), (8a') or (8e) are to be understood as a statistic description of the respective oligomeric radicals, that is to say, the orientation of the monomers and the sequence of the monomers (in case of copolymers) are not fixed in any way by said formulae. The arrangement of B and B' in formula (6a) or of the ethyleneoxide and propyleneoxide units in formula (6e) thus in each case may be random or blockwise.

The weight average molecular weight of the hydrophilic macromonomer for use in step (d) depends principally on the desired properties and is for example from 300 to 25000 Da, preferably from 300 to 12,000 Da, more preferably from 300 to 8000 Da, even more preferably from 300 to 5000 Da, and particularly preferably from 500 to 4000 Da.

The macromonomers of formula (6) may be prepared by methods known per se, as described in, for example, WO 99/57581.

The macromonomers of formula (6) may be applied to the initiator-modified bulk material surface and polymerized there according to processes known per se. For example, the bulk material is immersed in a solution of the macromonomer, or a layer of macromonomer is first of all deposited on the modified bulk material surface, for example, by dipping, spraying, spreading, knife coating, pouring, rolling, spin coating or vacuum vapor deposition. The polymerization of the macromonomer on the bulk material surface then may be initiated, for example, thermally by the action of heat or preferably by irradiation, particularly by UV radiation. Suitable light sources for the irradiation are known to the artisan and comprise for example mercury lamps, high-pressure mercury lamps, xenon lamps, carbon arc lamps or sunlight. The time period of irradiation may depend for example on the desired properties of the resulting composite material but is usually in the range of up to 30 minutes, preferably from 10 seconds to 10 minutes, and particularly preferably from 0.5 to 5 minutes. It is advantageous to carry out the irradiation in an atmosphere of inert gas. After the polymerization, any non-covalently bonded polymers, oligomers or non-reacted macromonomers formed can be removed, for example by treatment with suitable solvents.

By means of the above-described coating process, the macromonomers may be grafted to the bulk material surface with formation of a coating having for example a so-called bottle brush-type structure (BBT) composed of tethered "hairy" chains. Such BBT structures in one embodiment comprise a long hydrophilic or hydrophobic backbone, which carries relatively densely packed comparatively short hydrophilic side chains (called primary bottle brushes). Another embodiment relates to secondary bottle brushes which are characterized in that the hydrophilic side chains themselves carry densely packed hydrophilic "secondary" side chains. Polymeric coatings of said primary and secondary BBT structures to a certain extent mimic highly water-retaining structures occurring in the human body, for example in cartilage or mucosal tissue.

The coating thickness of the macromonomers depends principally on the desired properties. It can be, for example, from 0.001 to 1000 $\mu$m, preferably from 0.01 to 500 $\mu$m, more preferably from 0.01 to 100 $\mu$m, even more preferably from 0.05 to 50 $\mu$m, especially preferably from 0.1 to 5 $\mu$m and particularly preferably from 0.1 to 1 $\mu$m.

EXAMPLE A-1

Synthesis of a Photoinitiator with a Reactive Amino Group

A 1000 ml three-necked round bottom flask is charged with a solution of 224.26 g (1 Mol) of 4-(2-Hydroxyethoxy) phenyl 2-hydroxy-2-propyl-ketone (Darocure® 2959) in 400 mL of THF and 114.55 g (1 mol) of methanesulfonyl chloride are added to the solution at room temperature. After cooling to 2° C., 101.2 g (1 mol) of triethylamine (TEA) and 200 mL of THF are added to the solution over a 30 min-period under stirring. Slightly exothermal reaction is observed. The reaction mixture is then filtered through a G3 glass frit filter and the TEA hydrochloride washed 2× with THF on the filter. The filtrate is evaporated at 60° C./200 mbar using a Rotavapor. The resulting yellow oil is then dissolved in 800 mL of $CH_2Cl_2$. The organic phase is washed 1× with 400 mL of deionized water, 2× with 400 mL of acidic water (pH~1) and finally with 400 mL of deionized water. The organic phase is dried over $MgSO_4$, filtered and concentrated to constant weight by evaporating the $CH_2Cl_2$ under reduced pressure at a Rotavapor to give crude 4-(2-mesyloxyethoxy)phenyl-2-hydroxy-2-propyl-ketone.

10.1 g of the dried crude mesylate is dissolved in 30 mL of $CH_2Cl_2$. After addition of 50 g of ethanolamine, the mixture is heated to 80° C. and stirred at this temperature for 1 h. The unreacted ethanolamine is distilled off under reduced pressure and the product is dissolved in 100 mL of 2N HCl. After 20 min of stirring, the reaction mixture is extracted 2× with $CH_2Cl_2$. The aqueous layer is adjusted to pH 11 with 15% aqueous NaOH solution and extracted with $CH_2Cl_2$ (3×100 ml). The combined $CH_2Cl_2$ layers are dried over $MgSO_4$ and concentrated in vacuo. Crystallization of the residue from water (90° C.→4° C.) yields 2-hydroxy-2-methyl-1-[4-[2-hydroxyethylamino)ethoxy]phenyl]-1-propanone. The product is filtered off, dried and analyzed by $^1$H NMR-spectroscopy.

EXAMPLE A-2

Synthesis of a Photoinitiator with a Reactive Ester Group

The carboxylic acid 11 (f=1) is prepared as described in EP 0 281 941 A2 (Example 5, page 17). Acid 11 (v=1) is transformed to the corresponding N-hydroxysuccinimidyl ester

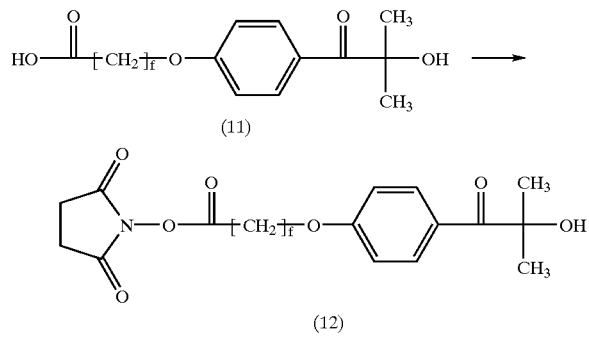

12 using the solid supported EDAC (ethyl dimethylaminopropylcarbodiimide) methodology described by Adamczyk, Fishpaugh and Mattingly in Tetrahedron Letters, Vol. 36, No. 46, pp. 8345–8346, 1995.

EXAMPLE B-1

Synthesis of Polyacrylic Acid with Pendant Photoinitiator Groups

To a solution of 28.8 g 25% aqueous polyacrylic acid ("PAA", Polysciences # 03326) diluted with 500 ml of deionized water is added 1.9 g (0.01 Mol) of 1-[3-(dimethylamino)propyl]-3-ethylcarbodiimide hydrochloride (Sigma-Aldrich # 161462) dissolved in 5 mL of deionized water, 2.1 g (0.01 mol) of N-hydroxysulfosuccinimide sodium salt ("sulfo-NHS", Fluka # 56485) dissolved in 5 mL of deionized water, and 2.67 g (0.01 mol) of the photoinitiator from Example A-1. The reaction mixture is adjusted to pH 9 by adding aqueous 1N NaOH solution and stirred at RT overnight. Subsequently, the pH is adjusted to 7 by adding 1N HCl. The product is purified by reverse osmosis, using Millipore cartridge with a cut-off at 1000 Da and then freeze-dried yielding 6.5 g of solid product. $^1$H NMR (300 MHz, D$_2$O) δ 7.00–7.10 (d, 2H); 8.15–8.25 (d, 2H) (aromatic protons of the photoinitiators bonded to PAA).

EXAMPLE B-2

Synthesis of Polyallylamine with Pendant Photoinitiator Groups

To a solution of 447 mg (1 mmol) of the photoinitiator prepared by the addition reaction of isophorone diisocyanate and 4-(2-hydroxyethoxy)phenyl 2-hydroxy-propyl ketone (Darocure® 2959) (synthesis see EP 0 632 329) in 5 mL of acetonitrile, is added 41.75 g of a 4.8% aqueous solution of polyallylamine (96.2% amino, 3.8% hydrochloride). After observing a slight opacity, additional 20 mL of acetonitrile are added to the reaction mixture. The reaction mixture is stirred at RT for 1 h and a further 10 mL of acetonitrile is added.

After this reaction time, IR spectroscopy showed no evidence of unreacted diisocyanate from the photoinitiator (O=C=N— at 2280 cm$^{-1}$). The slightly opaque solution is adjusted to pH 4.4 giving a clear solution and subsequently purified by reverse osmosis, using a Millipore cartridge with a cut-off at 1000 Da and freeze-dried to yield 2.5 g of a solid white product. $^1$H NMR (300 MHz, D$_2$O) δ 7.00–7.10 (d, 2H); 8.15–8.25 (d, 2H) (aromatic protons of the photoinitiators bonded to PAA).

EXAMPLE B-3

Synthesis of Hyaluronic Acid with Pendant Photoinitiator Groups

To a stirred solution of 4 g of hyaluronic acid (Denki Kagaku Kogyo, M$_n$~1.2×10$^6$ Da) dissolved in 800 mL of deionized water are subsequently added aqueous solutions of 1-[3-(dimethylamino)propyl]-3-ethylcarbodiimide hydrochloride (Sigma-Aldrich # 161462, 0.19 g in 5 mL of water) and of N-hydroxysulfosuccinimide sodium salt ("sulfo-NHS", Fluka # 56485, 0.14 g in 5 mL water). A solution of 120 mg of the photoinitiator described in Example A-1 in 10 mL of water is added to the reaction mixture. Subsequently, the reaction mixture is adjusted to pH 9 with 1N NaOH and stirred at RT overnight. After this reaction time, the pH is adjusted to 7 by adding 1N HCl. The mixture is purified by reverse osmosis, using a Millipore cartridge with a cut-off at 1000 Da and lyophilized, giving 4.1 g of a white product which carries a photoinitiator group bonded on about 3% of the sugar radicals in the main polymer chain, as shown by evaluation of the $^1$H-NMR spectrum. $^1$H chemical shifts of aromatic protons of the photoinitiators bonded to hyaluronic acid: δ 7.00–7.10 (d, 2H); 8.15–8.25 (d, 2H).

EXAMPLE B-4

Synthesis of Polyethylenimine with Pendant Photoinitiator Groups

A 100 mL three-necked round bottom flask equipped with thermometer, stirrer and condenser is charged with 5.508 g of a 50% aqueous solution of polyethylenimine (Fluka # 03880) and 50 ml of deionized water. To the stirred solution is slowly added 0.8 g (0.003 mol) of the photoinitiator with an active ester group (Example A-2, formula 12). The reaction mixture is stirred at 80° C. for 1 h. Subsequently, the mixture is cooled to RT, purified by reverse osmosis, using Millipore cartridge with a cut-off at 1000 Da and freeze-dried yielding 5.5 g of a solid product. $^1$H NMR (300 MHz, D$_2$O) δ 7.00–7.10 (d, 2H); 8.15–8.25 (d, 2H) (aromatic protons of the photoinitiators bonded to PAA).

EXAMPLE C-1

Preparation of Surface Functionalized Lenses by Deposition of a PAA Polymer Carrying Pendant Photoinitiator Groups a.) An approx. 0.001 M aqueous solution of a polyacrylic acid with pendant photoinitiator groups is prepared by dissolving 0.058 g of the polyacrylic acid with pendant photoinitiator groups from Example B-1 in 200 mL of ultra-pure water in a beaker, adjusting the pH of the solution to 2.5 by adding 1N HCl and filtering the solution through qualitative filter paper.

b.) An approx. 0.001 M polyallylamine hydrochloride ("PAH", Aldrich # 28.322-3) solution is prepared by adding 0.093 g PAH (solid) into a small beaker; dissolving in ultra-pure (UP) water and transferring into a bigger beaker with a final volume of 1000 mL aqueous solution. Adding 1 N HCl adjusts the pH to 4.5. The solution is then filtered through filter paper.

c.) Swollen non-coated Lotrafilcon A lenses (polysiloxane/perfluoroalkylpolyether copolymer) in isopropanol are individually immersed into the solution a.) for 5 minutes. The lenses are withdrawn from the solution a.) and directly immersed into the solution b.) for additional 5 min. The lenses are then withdrawn from the solution b.) and directly immersed again into the solution a. for additional 5 min.) No water rinse is done between these three dips. After that, the lenses are released into UP water and stored at 4° C. for further use.

EXAMPLE C-2

Preparation of Surface Functionalized Lenses by Deposition of Polymers Carrying Pendant Photoinitiator Groups a.) An approx. 0.001 M aqueous solution of a polyacrylic acid with pendant photoinitiator groups is prepared by adding 0.058 g of the polyacrylic acid with pendant photoinitiator groups from Example B-1 to 200 mL of ultra-pure water in a beaker. Subsequently, the pH of the solution is adjusted to 2.5 by adding 1N HCl and the solution is filtered using qualitative filter paper.

b.) A 0.001 M aqueous solution of a polyallylamine with pendant photoinitiator groups is prepared by adding 0.019 g of the polyallylamine with pendant photoinitiator groups from Example B-2 into a small beaker; dissolving in ultra-pure (UP) water and transferring into a bigger beaker with a final volume of 200 ml aqueous solution. The pH is then adjusted to 4.5 as measured by pH meter. The solution is then filtered using qualitative filter paper.

c.) Swollen non-coated Lotrafilcon A lenses in isopropanol are individually immersed into the solution a.) for 5 minutes. The lenses are withdrawn from the solution a.) and directly immersed into the solution b.) for additional 5 minutes. No water rinse is done between these two dips. After this, the lenses are released into UP water and stored at 4° C. for further use.

EXAMPLE C-3

Preparation of Surface Functionalized Lenses by Deposition of Polymers Carrying Pendant Photoinitiator Groups a.) An approx. 0.001 M aqueous solution of a polyacrylic acid with pendant photoinitiator groups is prepared by adding 0.289 g of the polyacrylic acid with pendant photoinitiator groups from example B-1 to 1000 mL of ultra-pure water in a beaker. Then the pH of the solution is adjusted to 2.5 by adding 1N HCl and the solution is filtered using qualitative filter paper b.) An approx. 0.001 M aqueous solution of a polyallylamine with pendant photoinitiator groups is prepared by adding 0.1 g of the polyallylamine with pendant photoinitiator groups from example B-2 into a small beaker; dissolving in ultra-pure (UP) water and transferring into a bigger beaker with a final volume of 1000 mL aqueous solution. The pH is then adjusted to 4.5 by adding 1N HCl as measured by pH meter. The solution is then filtered through filter paper.

c.) Swollen non-coated Lotrafilcon A lenses in isopropanol (IPA) are individually immersed into the solution a.) for 5 minutes. After this time, the lenses are withdrawn from the solution a.) and directly immersed into the solution b.) for additional 5 minutes. The lenses are than withdrawn from the solution b.) and directly immersed again into the solution a.) for additional 5 min. After this time, the lenses are withdrawn from the solution a.) and directly immersed into the solution b.) for additional 5 min. No water rinse is done between these four dips. After that, the lenses are released into UP water and stored at 4° C. for further use.

EXAMPLE C-4

Preparation of Surface Functionalized Lenses by Deposition of Polymers Carrying Pendant Photoinitiator Groups a.) An approx. 0.01% aqueous solution of a hyaluronic acid with pendant photoinitiator groups is prepared by adding 0.1 g of the hyaluronic acid with pendant photoinitiator groups from Example B-3 to 200 ml of water in a beaker. After complete dissolution (overnight), the pH of the solution is adjusted to 4.5 by adding 1N HCl and the solution is filtered trough a filter paper.

b.) 100 mL of an approx. 0.01% solution of polyethyleneimine with pendant photoinitiator groups is prepared by adding 0.01 g of the polyethyleneimine with pendant photoinitiator groups from Example B-4 into 200 mL of ultra-pure water. The pH is then adjusted to 3.5 by adding 1N HCl as measured by pH meter. The solution is then filtered using qualitative filter paper.

c.) Swollen non-coated Lotrafilcon A lenses in isopropanol (IPA) are individually immersed into the solution a.) for 10 min. The lenses are withdrawn from the solution a.) rinsed with ultra-pure water and immersed into the solution b.) for additional 10 min. After this, the lenses are released into ultra-pure water and stored at 4° C. for further use.

EXAMPLE D-1

Synthesis of an Acrylamide Telomer of $M_n$~1880

A 2000 mL round bottom flask is charged with a solution of 142.1 g (2 Mol) acrylamide (Fluka # 01696) in 700 mL of deionized water and cooled to −5° C. The frozen solution is evacuated to 50 mbar and after heating to RT filled with nitrogen gas. This freeze taw process is repeated three times.

1.1 g (4 mmol) of α,α'-azodiisobutyramidine dihydrochloride (Fluka 11633) and 17.5 g (0.154 mol) cysteamine hydrochloride (Fluka 30080) are added to the cooled solution under nitrogen atmosphere. The clear and slightly yellowish solution is acidified with a few drops of hydrochloric acid (32%) to pH 3.

With a constant stream of Argon, this solution is cooled to 5° C. and slowly introduced onto an 'flow-through-reactor' consisting of an 2000 mL three-necked round-bottom flask, reflux condenser, thermometer, magnetic stirrer and a 30 cm Liebig-condenser, filled with glass wool. The Liebig condenser is heated to 70° C., the flask is heated to 60° C. The cooled solution is slowly dropped through the Liebig-condenser into the stirred flask using the Chromatography Pump Büchi 681. This took 1 h 40 min. During this time the temperature in the flask is kept between 58–65° C. After the completed addition, the solution is stirred for 2 h at 60° C.

After cooling to RT, NaOH is added to the clear and slightly yellowish solution until pH 10.5 is reached. The product is purified through reverse osmosis, using Millipore cartridge with a cut-off at 1000 Da and freeze-dried. A bright-white solid product is obtained (87% yield). The concentration of amino groups is determined via functional group titration (0.53 mEq/g), which corresponds to $M_n$~1880 Da.

EXAMPLE D-2

Synthesis of an Acrylamide Telomer of $M_n$~1350

A 1000 mL round bottom flask is charged with a solution of 99.5 g (1.46 mol) acrylamide, 1.27 g (4.68 mmol) α,α'-azodiisobutyramidine dihydrochloride and 15.9 g (0.14 mol) cysteamine hydrochloride in 300 mL of water. The clear and slightly yellowish solution is acidified with a few drops of hydrochloric acid (32%) to pH 3. The stirred acidic solution is evacuated to 50 mbar and filled with argon. This is repeated three times. With a constant stream of argon, this solution is poured into a 500 mL dropping funnel which is put onto an 'flow-through-reactor' consisting of an 1000 mL three-necked round-bottom flask, reflux condenser, thermometer, magnetic stirrer and a 30 cm Liebig-condenser, which is filled with glass wool. The whole apparatus is constantly purged with Argon.

The dropping funnel is put onto the Liebig condenser, which is heated to 65° C. The flask is heated to 60° C. The solution is slowly dropped through the Liebig-condenser into the stirred flask. This takes 2 h. During this time the temperature in the flask is kept between 58–65° C. After the completed addition, the solution is stirred for 2 h at 60° C. Sodium hydroxide solution (30%) is added to the clear and slightly yellowish solution until pH 10 is reached. The product is purified through reverse osmosis, using Millipore cartridge with a cut-off at 1000 Da and then freeze-dried for 18 h. A bright-white solid product is obtained in 77% yield. The concentration of amino groups is determined via functional group titration (0.70 mEq/g), which corresponded well with the sulfur-value of the elemental analysis (0.73 mEq/g). $M_n$~1350 Da.

EXAMPLE D-3

Synthesis of an N,N-Dimethylacrylamide Telomer of $M_n$~1850

A 2000 mL round bottom flask is charged with a solution of 198.2 g (2 mol) Acrylamide, 2.72 g (10 mmol) α,α'-azodiisobutyramidine dihydrochloride and 24.8 g (0.22 mol) Cysteamine hydrochloride in 600 mL of water.

The clear and slightly yellowish solution is acidified with a few drops of hydrochloric acid (32%) to pH3. The stirred acidic solution is evacuated to 50 mbar and filled with argon. This is repeated three times. With a constant stream of Argon, this solution is poured into a 1000 mL dropping funnel which is put onto an 'flow-through-reactor' consisting of an 1000 mL three-necked round-bottom flask, reflux condenser, thermometer, magnetic stirrer and a 30 cm Liebig-condenser, which is filled with glass wool. The whole apparatus is constantly purged with Argon. The dropping funnel is put onto the Liebig condenser, which is heated to 60° C. The flask is also heated to 60° C. The solution is slowly dropped through the Liebig-condenser into the stirred flask. This takes 2.5 h. During this time the temperature in the flask is kept between 58–65° C. After the completed addition, the solution is stirred for 2 h at 60° C. Sodium hydroxide solution (30%) is added to the clear and slightly yellowish solution until pH 10 is reached. The product is purified through reverse osmosis, using Millipore cartridge with a cut-off at 1000 Da and freeze-dried. A bright-white solid product is obtained in 75% yield. The concentration of amino groups is determined via functional group titration (0.54 mEq/g). $M_n$~1850 Da.

EXAMPLE E-1

Preparation of IEM-functionalized Acrylamide Telomer Solution 7.5 g of acrylamide telomer with amino end group (amine titration=0.70 mEq/g), prepared by Example D-2 are dissolved in 50 ml of HPLC water. Argon is then let to bubble through the solution for the period of about 30 min. This mixture is then added to the equimolar amount (0.81 g) of isocyanatoethyl methacrylate (IEM, isocyanate titration=6.45 mEq/g) under stirring. The whole mixture is then stirred under argon flow for 12 h. After adding of 0.8 g of NaCl to the solution and 10 min stirring, the mixture is filtered through 0.45 μm Teflon filter, degassed by repeated (3×) evacuation and bubbling with argon in order to remove oxygen and used for photografting.

EXAMPLE E-2

Preparation of IEM-functionalized N,N-dimethylacrylamide Telomer Solution 5 g of N,N-dimethylacrylamide telomer with amino end group (amine titration=0.53 mEq/g), prepared by Example D-3 are dissolved in 100 mL of HPLC water. Argon is then let to bubble through the solution for the period of about 30 min. This mixture is then added to the equimolar amount (0.41 g) of isocyanatoethyl methacrylate (IEM, isocyanate titration=6.45 mEq/g) under stirring. The whole mixture is then stirred under argon flow for 12 h. After adding of 1.0 g of NaCl to the solution and 10 minutes stirring, the mixture is filtered through 0.45 μm Teflon filter, degassed with nitrogen in order to remove oxygen and used for photografting.

EXAMPLE E-3

Preparation of IEM-functionalized N,N-dimethylacrylamide Telomer Solution 15 g of N,N-dimethylacrylamide telomer with amino end group (amine titration=0.53 mEq/g), prepared by Example D-3 are dissolved in 100 mL of HPLC water. Argon is then let to bubble through the solution for the period of about 30 min. This mixture is then added to the equimolar amount (1.23 g) of isocyanatoethyl methacrylate (IEM, isocyanate titration=6.45 mEq/g) under stirring. The whole mixture is then stirred under argon flow for 12 h. After adding of 1.0 g of NaCl to the solution and 10 min stirring, the mixture is filtered through 0.45 μm Teflon filter, degassed with nitrogen in order to remove oxygen and used for photografting.

EXAMPLE E-4

Preparation of IEM-functionalized Acrylamide Telomer Solution 7.5 g of acrylamide telomer with amino end group (amine titration=0.53 mEq/g), prepared by Example D-1 are dissolved in 40 mL of HPLC water. Argon is then let to bubble through the solution for the period of about 30 min. This mixture is then added to the equimolar amount (0.61 g) of isocyanatoethyl methacrylate (IEM, isocyanate titration=6.45 mEq/g) under stirring. The whole mixture is then stirred under argon flow for 12 h. After adding of 0.8 g of NaCl to the solution and 10 min stirring, the mixture is filtered through 0.45 tm Teflon filter, degassed by repeated (3×) evacuation and bubbling with argon in order to remove oxygen and used for photografting.

EXAMPLE E-5

Preparation of IEM-functionalized Acrylamide Telomer Solution 6.45 g of acrylamide telomer with amino end group (amine titration=0.53 mEq/g), prepared by Example D-1 are dissolved in 65 mL of HPLC water. Argon is then let to bubble through the solution for the period of about 30 min. This mixture is then added to the equimolar amount (0.0.53 g) of isocyanatoethyl methacrylate (IEM, isocyanate titration=6.45 mEq/g) under stirring. The whole mixture is then stirred under argon flow for 12 h. After adding of 1.3 g of NaCl to the solution and 10 min stirring, the mixture is filtered through 0.45 µm Teflon filter, degassed by repeated (3×) evacuation and bubbling with argon in order to remove oxygen and used for photografting.

EXAMPLE F-1

Photografting of IEM-functionalized Acrylamide Telomers Onto a Contact Lens Surface 1 ml of the IEM-functionalized acrylamide telomer solution from Example E-1 is introduced into a small Petri dish of a volume of about 2 mL. The lens from Example C-1, carrying covalently linked photoinitiator molecules on its surface, is then placed into this solution and an additional 0.5 mL of the degassed solution is added on the lens in order to cover the whole lens with the solution. After 10 min, the Petri dish with the lens in the solution is exposed to 3.34 mW/cm$^2$ ultraviolet light for a period of 2 min.

The modified lens is then withdrawn from the solution, washed twice in distilled water, continuously extracted in ultra pure water for 16 h and analyzed by AFM, ATR-FTIR and contact angle measurements.

Water/air contact angles on the modified lens are 0° adv., 0° rec., 0° hysteresis. In comparison, the contact angles of non-modified lens are 101° adv., 64°rec., 37° hysteresis. The lens held continuous water layer on the surface for over 1 min.

EXAMPLE F-2

Photografting of IEM-functionalized Acrylamide Telomers Onto a Contact Lens Surface Two lenses from Example C-1 are coated in accordance with Example F-1, but instead of 2 min of exposition, 3 min exposition time is used for photografting.

Water/air contact angles on the modified lenses are 33° adv., 26° rec., 7° hysteresis.

EXAMPLE F-3

Photografting of IEM-functionalized N,N-dimethylacrylamide Telomers Onto a Contact Lens Surface 1 ml of the IEM-functionalized N,N-dimethylacrylamide telomer solution from Example E-2 is introduced into a small Petri dish of a volume of about 2 mL in a glove box. The lens from Example C-3, carrying covalently linked photoinitiator molecules on its surface, is then placed into this solution and an additional 0.5 mL of the degassed solution is added on the lens in order to cover the whole lens with the solution. After 10 min, the Petri dish with the lens in the solution is exposed to 14.5 mW/cm$^2$ ultraviolet light for a period of 1.5 min. The lens is then turned over and the exposition is repeated by applying 14.5 mW/cm$^2$ UV light for an additional 1.5 min.

The modified lens is then withdrawn from the solution, washed twice in distilled water, continuously extracted in ultra pure water for 16 h and analyzed by AFM, ATR-FTIR and contact angle measurements.

Water/air contact angles on the modified lens are 11° adv., 3° rec., 8° hysteresis. In comparison, the contact angles of non-modified lens are 101° adv., 64° rec., 37° hysteresis.

EXAMPLE F-4

Photografting of IEM-functionalized Acrylamide Telomers Onto a Contact Lens Surface Under Ambient Conditions In a laminar flow hood, 1 mL of the IEM-functionalized acrylamide telomer solution from Example E-4 is introduced into a small Petri dish of a volume of about 2 mL. The lens from Example C-1, carrying covalently linked photoinitiator molecules on its surface, is then placed into this solution and an additional 0.5 mL of the degassed solution is added on the lens in order to cover the whole lens with the solution. After 10 min, the Petri dish with the lens in the solution is exposed to ultraviolet light 3.34 mW/cm$^2$ (MACAM-UV-Lamp) for a period of 2 min. The modified lens is then withdrawn from the solution, washed twice in distilled water, continuously extracted in ultra pure water for 16 h and analyzed by AFM, ATR-FTIR and contact angle measurements.

The thickness of the coating is in the range of 100–200 nm as determined by AFM.

Water/air contact angles on the modified lens are 0° adv., 0° rec., 0° hysteresis. In comparison, the contact angles of non-modified lens are 101° adv., 64° rec., 37° hysteresis. The lens held continuous water layer on the surface for over 1 min.

EXAMPLE F-5

Photografting of IEM-functionalized Acrylamide Telomers Onto a Contact Lens Surface Two lenses from Example C-1 are coated in accordance with Example F-4, but instead of 2 min of exposition, 1.5 min exposition time is used for photografting with UV energy 2.4 mW/cm$^2$.

Water/air contact angles on the modified lenses are 0° adv., 0° rec., 0° hysteresis.

EXAMPLE F-6

Photografting of IEM-functionalized Acrylamide Telomers Onto a Contact Lens Surface 1 mL of the IEM-functionalized acrylamide telomer solution from Example E-5 is introduced into a small Petri dish of a volume of about 2.5 mL in a glove box. The lens from Example C-4, carrying covalently linked photoinitiator molecules on its surface, is then placed into this solution and an additional 1 ml of the degassed solution is added on the lens in order to cover the whole lens with the solution. After 10 min, the Petri dish with the lens in the solution is exposed to 14.5 mW/cm$^2$ ultraviolet light for a period of about 3 min.

The modified lens is then withdrawn from the solution, washed twice in distilled water, continuously extracted in ultra pure water for 16 h and analyzed by ATR-FTIR and contact angle measurements.

Water/air contact angles on the modified lens are 33° adv., 10° rec., 23° hysteresis. In comparison, the contact angles of non-modified lens are 101° adv., 64° rec., 37° hysteresis.

EXAMPLE F-7

Photografting of IEM-functionalized Acrylamide Telomers Onto a Contact Lens Surface 1 ml of the IEM-functionalized acrylamide telomer solution from Example E-5 is introduced into a small Petri dish of a volume of about 2.5 mL in a glove box. The lens from Example C-2, carrying covalently linked photoinitiator molecules on its surface, is then placed into this solution and an additional 1 mL of the degassed solution is added on the lens in order to cover the whole lens with the solution. After 10 min, the Petri dish with the lens in the solution is exposed to 14.5 mW/cm² ultraviolet light for a period of about 7 min.

The modified lens is then withdrawn from the solution, washed twice in distilled water, continuously extracted in ultra pure water for 16 h and analyzed by ATR-FTIR and contact angle measurements.

Water/air contact angles on the modified lens are 0° adv., 0° rec., 0° hysteresis. In comparison, the contact angles of non-modified lens are 101° adv., 64° rec., 37° hysteresis.

What is claimed is:

1. A process for coating a material surface, comprising the steps of:

(a) providing an inorganic or organic bulk material;

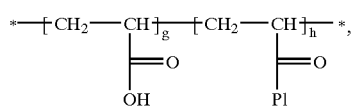

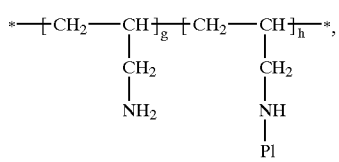

(b) providing one or more polyionic materials at least one of them comprising covalently bound initiator moieties for radical polymerization;
    (c) applying the polyionic material of step (b) to the bulk material of step (a), thereby forming a hydrophilic layer on the bulk material surface; and
    (d) graft polymerizing a hydrophilic monomer or macromonomer onto said polyionic material.

2. A process according to claim 1, wherein the material surface is the surface of a biomedical device comprising an organic bulk material.

3. A process according to claim 2, wherein the material surface is the surface of a contact lens, intraocular lens or artificial cornea.

4. A process according to claim 3, wherein in step (b), a polyionic material comprising covalently bound initiator moieties for radical polymerization is derived from the group consisting of polyacrylic acid, polyethyleneimine, polyallylamine and hyaluronic acid.

5. A process according to claim 4, wherein in step (b), the polyionic material comprises structural units of formula

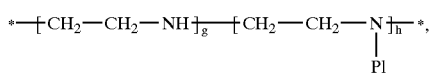

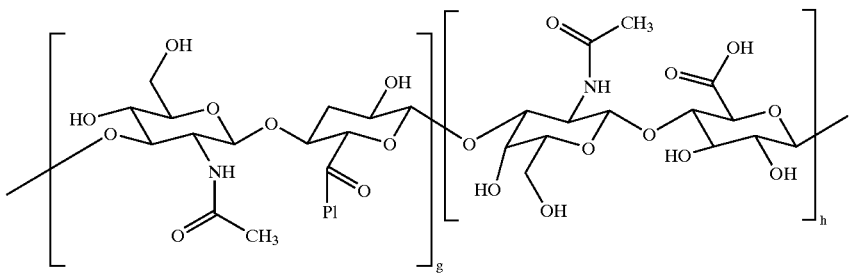

wherein
the ratio of g:h is from 1:10 to 1:200,
the total of (g+h) is an integer from 10 to 25000;
and PI is the radical of a photoinitiator.

6. A process according to claim 4, wherein in step (b), the polyionic material comprises structural units of formula

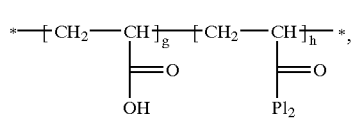

-continued

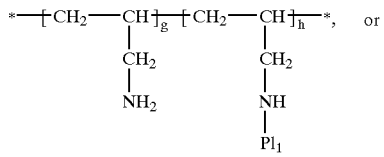

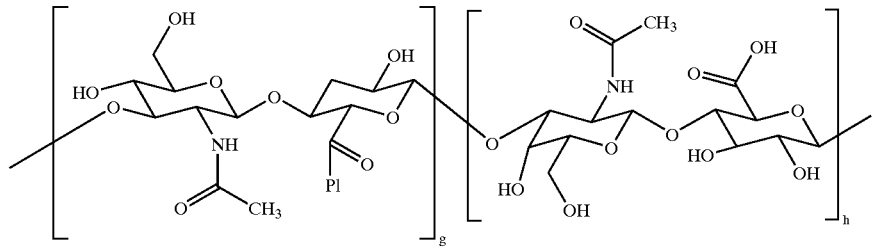

wherein
the ratio of g:h is from 1:10 to 1:200,
the total of (g+h) is an integer from 10 to 25000;
$PI_1$ is a radical of formula

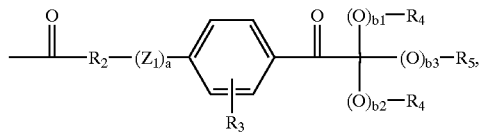

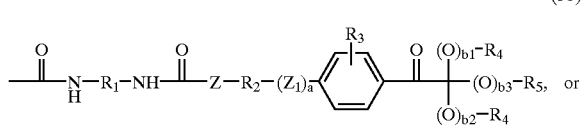

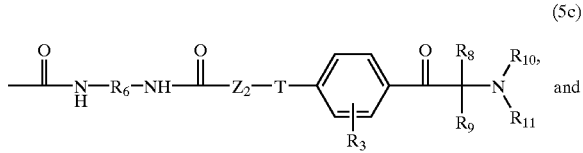

$PI_2$ is a radical of formula

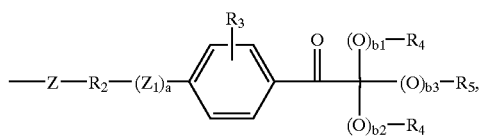

wherein Z is bivalent —O—, —NH— or —$NR_{12}$—; $Z_1$ is —O—, —O—(O)C—, —C(O)—O— or —O—C(O)—O—; $R_3$ is H, $C_1$–$C_{12}$-alkyl, $C_1$–$C_{12}$-alkoxy or N—$C_1$–$C_{12}$-alkylamino; $R_4$ and $R_5$ are each independently of the other H, linear or branched $C_1$–$C_8$-alkyl, $C_1$–$C_8$-hydroxyalkyl or $C_6$–$C_{10}$-aryl, or the groups $R_4$—(O)$_{b1}$— and $R_4$—(O)$_{b2}$— together are —(CH$_2$)$_c$— wherein c is an integer from 3 to 5, or the groups $R_4$—(O)$_{b1}$—, $R_4$—(O)$_{b2}$— and $R_5$—(O$_1$)$_{b3}$— together are a radical of the formula

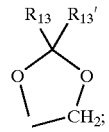

$R_2$ is a direct bond or linear or branched $C_1$–$C_8$-alkylene that is unsubstituted or substituted by —OH and/or is uninterrupted or interrupted by one or more groups —O—, —O—C(O)— or —O—C(O)—O—; $R_1$ is branched $C_3$–$C_{18}$-alkylene, unsubstituted or $C_1$–$C_4$-alkyl- or $C_1$–$C_4$-alkoxy-substituted $C_6$–$C_{10}$-arylene, or unsubstituted or $C_1$–$C_4$-alkyl- or $C_1$–$C_4$-alkoxy-substituted $C_7$–$C_{18}$-aralkylene, unsubstituted or $C_1$–$C_4$-alkyl- or $C_1$–$C_4$-alkoxy-substituted $C_3$–$C_8$-cycloalkylene, unsubstituted or $C_1$–$C_4$-alkyl- or $C_1$–$C_4$-alkoxy-substituted $C_3$–$C_8$-cycloalkylene-$C_yH_{2y}$— or unsubstituted or $C_1$–$C_4$-alkyl- or $C_1$–$C_4$-alkoxy-substituted $C_yH_{2y}$—($C_3$–$C_8$-cycloalkylene)-$C_yH_{2y}$— wherein y is an integer from 1 to 6; $R_6$ independently has the same definitions as $R_1$ or is linear $C_3$–$C_{18}$-alkylene; $R_{12}$ is linear or branched $C_1$–$C_6$-alkyl which may be further substituted, for example by hydroxy; T is bivalent —O—, —NH—, —S—, $C_1$–$C_8$-alkylene or

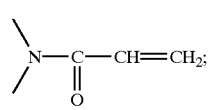

$Z_2$ is a direct bond or —O—(CH$_2$)$_d$— or —(OCH$_2$CH$_2$)$_d$— wherein d is an integer from 1 to 6 and the terminal CH$_2$ group of which is each linked to the adjacent T in formula (3c); $R_8$ is linear or branched $C_1$–$C_8$-alkyl, $C_2$–$C_8$-alkenyl or $C_6$–$C_{10}$-aryl-$C_1$–$C_8$-alkyl; $R_9$ independently of $R_8$ has the same definitions as $R_8$ or is $C_6$–$C_{10}$-aryl, or $R_8$ and $R_9$ together are —(CH$_2$)$_e$— wherein e is an integer from 2 to 6; $R_{10}$ and $R_{11}$ are each independently of the other linear or branched $C_1$–$C_8$-alkyl that may be substituted by $C_1$–$C_4$-alkoxy, or $C_6$–$C_{10}$-aryl-$C_1$–$C_8$-alkyl or $C_2$–$C_8$-alkenyl; or $R_{10}$ and $R_{11}$ together are —(CH$_2$)$_{f1}$—$Z_3$—(CH$_2$)$_{f2}$— wherein $Z_3$ is a direct bond, —O—, —S— or —$NR_7$—, and $R_7$ is H or $C_1$–$C_8$-alkyl and f1 and f2 are each independently of the other an integer from 2 to 4; $R_{13}$ and $R_{13}$' are each independently of the other H, $C_1$–$C_8$-alkyl, $C_3$–$C_8$- cycloalkyl, benzyl or phenyl; and a, a1, b1, b2 and b3 are each independently of the other 0 or 1; subject to the provisos that b1 and b2 are each 0 when $R_{15}$ is H; that the total of (b1+b2+b3) is not exceeding 2; and that a is 0 when $R_{12}$ is a direct bond.

7. A process according to claim 1, wherein a macromonomer of formula

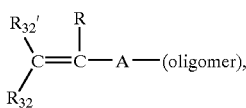 (6)

is applied in step (d), wherein $R_{32}$ is hydrogen, $C_1$–$C_6$-alkyl or a radical —COOR';

R, R' and $R_{32}'$ are each independently of the other hydrogen or $C_1$–$C_6$-alkyl;

A is a direct bond or is a radical of formula

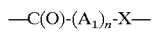 (7a) or

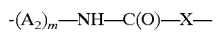 (7b); or

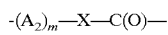 (7c); or

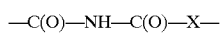 (7d); or

 (7e); or

A and $R_{32}$, together with the adjacent double bond, are a radical of formula

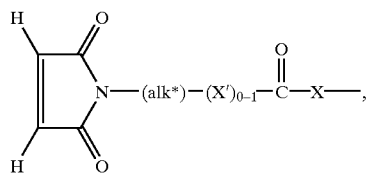 (7f)

$A_1$ is —O—$C_2$–$C_{12}$-alkylene which is unsubstituted or substituted by hydroxy, or is —O—$C_2$–$C_{12}$-alkylene-NH—C(O)— or —O—$C_2$–$C_{12}$-alkylene-O—C(O)—NH—$R_{33}$—NH—C(O)— or —NH-(Alk*)-C(O)—, wherein (Alk*) is $C_1$–$C_6$-alkylene and $R_{33}$ is linear or branched $C_1$–$C_{18}$-alkyl or unsubstituted or $C_1$–$C_4$-alkyl- or $C_1$–$C_4$-alkoxy-substituted $C_6$–$C_{10}$-arylene, $C_7$–$C_{18}$-aralkylene, $C_6$–$C_{10}$-arylene-$C_1$–$C_2$-alkylene-$C_6$–$C_{10}$-arylene, $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene;

$A_2$ is $C_1$–$C_8$-alkylene; phenylene or benzylene;

m and n are each independently of the other the number 0 or 1;

X, $X_1$ and X' are each independently of the other a bivalent group —O— or —NR", wherein R" is hydrogen or $C_1$–$C_6$-alkyl;

(alk*) is $C_2$–$C_{12}$-alkylene;

and (oligomer) denotes (i) the radical of a telomer of formula

 (8a)

wherein (alk) is $C_2$–$C_{12}$-alkylene,

Q is a monovalent group that is suitable to act as a polymerization chain-reaction terminator, p and q are each independently of another an integer from 0 to 350, wherein the total of (p+q) is an integer from 2 to 350, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (ii) the radical of an oligomer of the formula

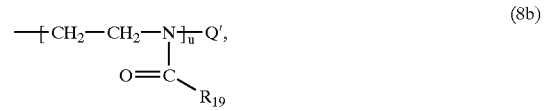 (8b)

wherein $R_{19}$ is hydrogen or unsubstituted or hydroxy-substituted $C_1$–$C_{12}$-alkyl, u is an integer from 2 to 250 and Q' is a radical of a polymerization initiator; or (iii) the radical of formula

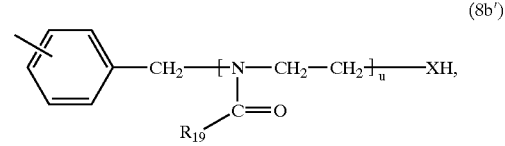 (8b')

wherein $R_{19}$, X and u are as defined above, or (iv) the radical of an oligomer of formula

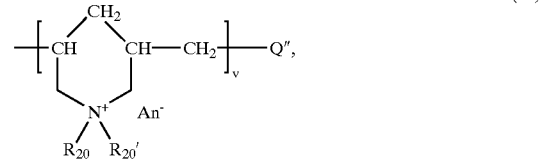 (8c)

wherein $R_{20}$ and $R_{20}'$ are each independently $C_1$–$C_4$-alkyl, $An^-$ is an anion, v is an integer from 2 to 250, and Q" is a monovalent group that is suitable to act as a polymerization chain-reaction terminator; or (v) the radical of an oligopeptide of formula

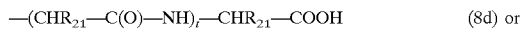 (8d) or

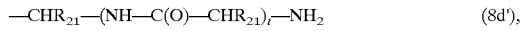 (8d'), wherein $R_{21}$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—$NH_2$ and t is an integer from 2 to 250, or the radical of an oligopeptide based on proline or hydroxyproline; or (vi) the radical of a polyalkylene oxide of formula

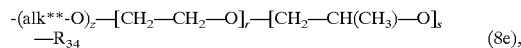

wherein $R_{34}$ is hydrogen or $C_1-C_{24}$-alkyl, (alk**) is $C_2-C_4$-alkylene, z is 0 or 1, r and s are each independently an integer from 0 to 250 and the total of (r+s) is from 2 to 250; or (vii) the radical of an oligosaccharide;
subject to the provisos that
A is not a direct bond if (oligomer) is a radical of formula (6a);

A is a radical of formula (7a), (7b) or (7d) or A and $R_{32}$, together with the adjacent double bond, are a radical of formula (7f) if (oligomer) is a radical of formula (8b), (8c), (8d) or (8e) or is the radical of an oligosaccharide;
A is a direct bond if (oligomer) is a radical of formula (8b'); and
A is a radical of formula (7c) or (7e) if (oligomer) is a radical of formula (8d').

8. A process according to claim 7, wherein R is hydrogen or methyl, $R_{32}$ and $R_{32}'$ are each hydrogen, A is a radical of the formula (5a) and (oligomer) is a radical of formula (8a).

9. A process according to claim 7, wherein (oligomer) is a radical of formula

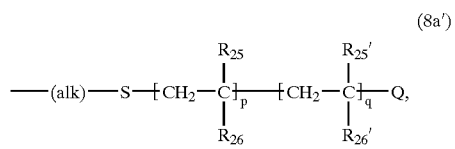

wherein (alk) is $C_2-C_4$-alkylene, $R_{25}$ and $R_{25}'$ are each independently hydrogen or methyl, Q is a monovalent group that is suitable to act as a polymerization chain-reaction terminator, p and q are each independently an integer from 0 to 100 wherein the total of (p+q) is an integer from 5 to 100, and $R_{26}$ and $R_{26}'$ are each independently a radical —COOY, wherein Y is $C_1-C_2$-alkyl, $C_2-C_3$-alkyl, which is substituted by hydroxy, amino or N,N-di-$C_1-C_2$-alkyl-amino, or is a radical —$C_2-C_4$-alkylene-NH—C(O)—O-G wherein —O-G is the radical of trehalose; a radical —CO—$NY_1Y_2$, wherein $Y_1$ and $Y_2$ are each independently of the other hydrogen or $C_1-C_2$-alkyl which is unsubstituted or substituted by hydroxy, or $Y_1$ and $Y_2$ together with the adjacent N-atom form a N—$C_1-C_2$-alkylpiperazino or morpholino ring; a heterocyclic radical selected from the group consisting of N-pyrrolidonyl, 2- or 4-pyridinyl, 2-methylpyridin-5-yl, 2-, 3-oder 4-hydroxypyridinyl, N-ε-caprolactamyl, N-imidazolyl, 2-methylimidazol-1-yl, N-morpholinyl and 4-N-methylpiperazin-1-yl; —COOH; —$SO_3H$; o-, m- or p-sulfophenyl; o-, m- or p-sulfomethylphenyl; a radical —$CONY_5Y_6$ wherein $Y_5$ is $C_2-C_4$-alkyl substituted by sulfo, and $Y_6$ is hydrogen; $C_1-C_4$-alkyl which is substituted by —$NR_{23}R_{23}'R_{23}''^+An^-$ wherein $R_{23}$, $R_{23}'$ and $R_{23}''$ are each independently of another hydrogen or $C_1-C_4$-alkyl and $An^-$ is an anion; a radical —$C(O)OY_7$ wherein $Y_7$ is $C_2-C_4$-alkyl, which is substituted by —$NR_{23}R_{23}'R_{23}''^+An^-$ and is further unsubstituted or substituted by hydroxy, wherein $R_{23}$, $R_{23}'$, $R_{23}''$ and $^+An^-$ are as defined; and a radical —C(O)O—$CH_2$—CH($OY_8$)—$CH_2$—O—$PO_2^-$—$(CH_2)_2$—$N(CH_3)_3^+$, wherein $Y_8$ is hydrogen or the acyl radical of a higher fatty acid.

10. A process according to claim 1, wherein in step (d) a macromonomer of formula

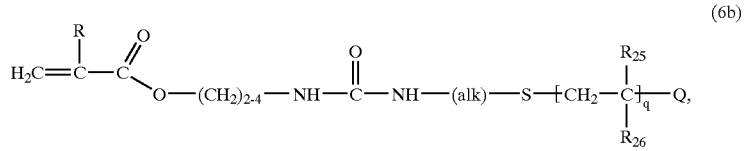

is applied, wherein R is hydrogen or methyl, (alk) is $C_2-C_4$-alkylene, $R_{25}$ is hydrogen or methyl, p is an integer of 5 to 50, Q is a monovalent group that is suitable to act as a polymerization chain-reaction terminator, and $R_{26}$ is a radical —$CONH_2$, —$CON(CH_3)_2$ or

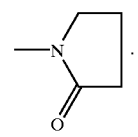

11. A coated material that is obtained by the process of claim 1.

12. A coated material according to claim 11, which is a biomedical device.

13. A coated material according to claim 12, which is a biomedical device.

14. A coated material according to claim 13, which is a contact lens, intraocular lens or an artificial cornea.

15. A process according to claim 3, wherein a macromonomer of formula

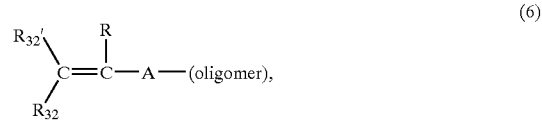

is applied in step (d),
wherein $R_{32}$ is hydrogen, $C_1-C_6$-alkyl or a radical —COOR';
R, R' and $R_{32}'$ are each independently of the other hydrogen or $C_1-C_6$-alkyl;
A is a direct bond or is a radical of formula

| —C(O)-(A$_1$)$_n$-X— | (7a) or |
| -(A$_2$)$_m$—NH—C(O)—X— | (7b); or |
| -(A$_2$)$_m$—X—C(O)— | (7c); or |
| —C(O)—NH—C(O)—X— | (7d); or |
| —C(O)—X$_1$-(alk*)-X—C(O)— | (7e); or |

A and $R_{32}$, together with the adjacent double bond, are a radical of formula

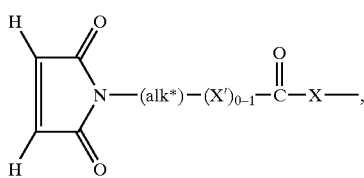

(7f)

$A_1$ is —O—$C_2$–$C_{12}$-alkylene which is unsubstituted or substituted by hydroxy, or is —O—$C_2$–$C_{12}$-alkylene-NH—C(O)— or —O—$C_2$–$C_{12}$-alkylene-O—C(O)—NH—$R_{33}$—NH—C(O)— or —NH-(Alk*)-C(O)—, wherein (Alk*) is $C_1$–$C_6$-alkylene and $R_{33}$ is linear or branched $C_1$–$C_{18}$-alkylene or unsubstituted or $C_1$–$C_4$-alkyl- or $C_1$–$C_4$-alkoxy-substituted $C_6$–$C_{10}$-arylene, $C_7$–$C_{18}$-aralkylene, $C_6$–$C_{10}$-arylene-$C_1$–$C_2$-alkylene-$C_6$–$C_{10}$-arylene, $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene;

$A_2$ is $C_1$–$C_8$-alkylene; phenylene or benzylene;

m and n are each independently of the other the number 0 or 1;

X, $X_1$ and X' are each independently of the other a bivalent group —O— or —NR″, wherein R″ is hydrogen or $C_1$–$C_6$-alkyl;

(alk*) is $C_2$–$C_{12}$-alkylene;

and (oligomer) denotes (i) the radical of a telomer of formula

(8a)

wherein (alk) is $C_2$–$C_{12}$-alkylene,

Q is a monovalent group that is suitable to act as a polymerization chain-reaction terminator, p and q are each independently of another an integer from 0 to 350, wherein the total of (p+q) is an integer from 2 to 350, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (ii) the radical of an oligomer of the formula

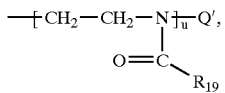

(8b)

wherein $R_{19}$ is hydrogen or unsubstituted or hydroxy-substituted $C_1$–$C_{12}$-alkyl, u is an integer from 2 to 250 and Q' is a radical of a polymerization initiator; or (iii) the radical of formula

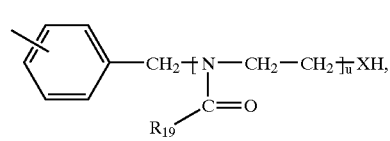

(8b')

wherein $R_{19}$, X and u are as defined above, or (iv) the radical of an oligomer of formula

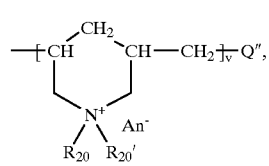

(8c)

wherein $R_{20}$ and $R_{20}'$ are each independently $C_1$–$C_4$-alkyl, An⁻ is an anion, v is an integer from 2 to 250, and Q″ is a monovalent group that is suitable to act as a polymerization chain-reaction terminator; or (v) the radical of an oligopeptide of formula

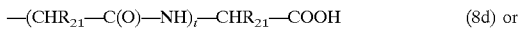

(8d) or

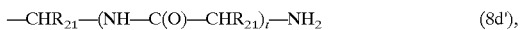

(8d'), wherein $R_{21}$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—$NH_2$ and t is an integer from 2 to 250, or the radical of an oligopeptide based on proline or hydroxyproline; or (vi) the radical of a polyalkylene oxide of formula

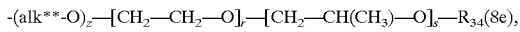

wherein $R_{34}$ is hydrogen or $C_1$–$C_{24}$-alkyl, (alk**) is $C_2$–$C_4$-alkylene, z is 0 or 1, r and s are each independently an integer from 0 to 250 and the total of (r+s) is from 2 to 250; or (vii) the radical of an oligosaccharide;

subject to the provisos that

A is not a direct bond if (oligomer) is a radical of formula (6a);

A is a radical of formula (7a), (7b) or (7d) or A and $R_{32}$, together with the adjacent double bond, are a radical of formula (7f) if (oligomer) is a radical of formula (8b), (8c), (8d) or (8e) or is the radical of an oligosaccharide;

A is a direct bond if (oligomer) is a radical of formula (8b'); and

A is a radical of formula (7c) or (7e) if (oligomer) is a radical of formula (8d').

16. A process according to claim 4, wherein a macromonomer of formula

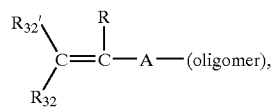

(6)

is applied in step (d), wherein $R_{32}$ is hydrogen, $C_1$–$C_6$-alkyl or a radical —COOR';

R, R' and $R_{32}$' are each independently of the other hydrogen or $C_1$–$C_6$-alkyl;

A is a direct bond or is a radical of formula

—C(O)-($A_1$)$_n$-X—     (7a) or

-($A_2$)$_m$—NH—C(O)—X—     (7b); or

-($A_2$)$_m$—X—C(O)—     (7c); or

—C(O)—NH—C(O)—X—     (7d); or

—C(O)—$X_1$-(alk*)-X—C(O)—     (7e); or

A and $R_{32}$, together with the adjacent double bond, are a radical of formula

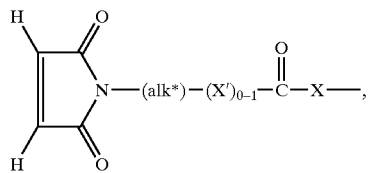
(7f)

$A_1$ is —O—$C_2$–$C_{12}$-alkylene which is unsubstituted or substituted by hydroxy, or is —O—$C_2$–$C_{12}$-alkylene-NH—C(O)— or —O—$C_2$–$C_{12}$-alkylene-O—C(O)—NH—$R_{33}$—NH—C(O)— or —NH-(Alk*)-C(O)—, wherein (Alk*) is $C_1$–$C_6$-alkylene and $R_{33}$ is linear or branched $C_1$–$C_{18}$-alkylene or unsubstituted or $C_1$–$C_4$-alkyl- or $C_1$–$C_4$-alkoxy-substituted $C_6$–$C_{10}$-arylene, $C_7$–$C_{18}$-aralkylene, $C_6$–$C_{10}$-arylene-$C_1$–$C_2$-alkylene-$C_6$–$C_{10}$-arylene, $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene;

$A_2$ is $C_1$–$C_8$-alkylene; phenylene or benzylene;

m and n are each independently of the other the number 0 or 1;

X, $X_1$ and X' are each independently of the other a bivalent group —O— or —NR", wherein R" is hydrogen or $C_1$–$C_6$-alkyl;

(alk*) is $C_2$–$C_{12}$-alkylene;

and (oligomer) denotes (i) the radical of a telomer of formula

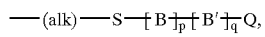
(8a)

wherein (alk) is $C_2$–$C_{12}$-alkylene,

Q is a monovalent group that is suitable to act as a polymerization chain-reaction terminator, p and q are each independently of another an integer from 0 to 350, wherein the total of (p+q) is an integer from 2 to 350, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (ii) the radical of an oligomer of the formula

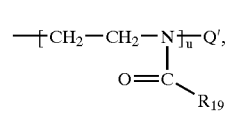
(8b)

wherein $R_{19}$ is hydrogen or unsubstituted or hydroxy-substituted $C_1$–$C_{12}$-alkyl, u is an integer from 2 to 250 and Q' is a radical of a polymerization initiator; or (iii) the radical of formula

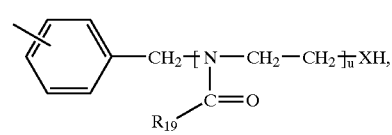
(8b')

wherein $R_{19}$, X and u are as defined above, or (iv) the radical of an oligomer of formula

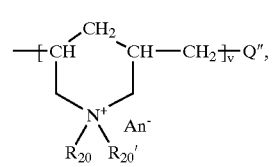
(8c)

wherein $R_{20}$ and $R_{20}$' are each independently $C_1$–$C_4$-alkyl, An⁻ is an anion, v is an integer from 2 to 250, and Q" is a monovalent group that is suitable to act as a polymerization chain-reaction terminator; or (v) the radical of an oligopeptide of formula —(CHR$_{21}$—C(O)—NH)$_t$—CHR$_{21}$—COOH     (8d) or —CHR$_{21}$—(NH—C(O)—CHR$_{21}$)$_t$—NH$_2$     (8d'), wherein $R_{21}$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—NH$_2$ and t is an integer from 2 to 250, or the radical of an oligopeptide based on proline or hydroxyproline; or (vi) the radical of a polyalkylene oxide of formula -(alk-O)$_z$—[CH$_2$—CH$_2$—O]$_r$—[CH$_2$—CH(CH$_3$)—O]$_s$—R$_{34}$(8e), wherein $R_{34}$ is hydrogen or $C_1$–$C_{24}$-alkyl, (alk) is $C_2$–$C_4$-alkylene, z is 0 or 1, r and s are each independently an integer from 0 to 250 and the total of (r+s) is from 2 to 250; or (vii) the radical of an oligosaccharide;

subject to the provisos that

A is not a direct bond if (oligomer) is a radical of formula (6a);

A is a radical of formula (7a), (7b) or (7d) or A and $R_{32}$, together with the adjacent double bond, are a radical of formula (7f) if (oligomer) is a radical of formula (8b), (8c), (8d) or (8e) or is the radical of an oligosaccharide;

A is a direct bond if (oligomer) is a radical of formula (8b'); and

A is a radical of formula (7c) or (7e) if (oligomer) is a radical of formula (8d').

17. A process according to claim 5, wherein a macromonomer of formula

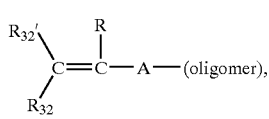     (6)

is applied in step (d), wherein $R_{32}$ is hydrogen, $C_1$–$C_6$-alkyl or a radical —COOR';

R, R' and $R_{32}'$ are each independently of the other hydrogen or $C_1$–$C_6$-alkyl;

A is a direct bond or is a radical of formula

—C(O)-(A$_1$)$_n$-X—      (7a) or

-(A$_2$)$_m$—NH—C(O)—X—      (7b); or

-(A$_2$)$_m$—X—C(O)—      (7c); or

—C(O)—NH—C(O)—X—      (7d); or

—C(O)—X$_1$-(alk*)-X—C(O)—      (7e); or

A and $R_{32}$, together with the adjacent double bond, are a radical of formula

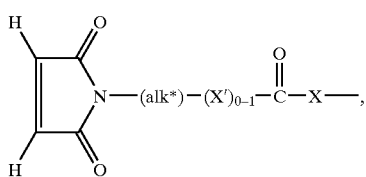     (7f)

$A_1$ is —O—$C_2$–$C_{12}$-alkylene which is unsubstituted or substituted by hydroxy, or is —O—$C_2$–$C_{12}$-alkylene-NH—C(O)— or —O—$C_2$–$C_{12}$-alkylene-O—C(O)—NH—$R_{33}$—NH—C(O)— or —NH-(Alk*)-C(O)—, wherein (Alk*) is $C_1$–$C_6$-alkylene and $R_{33}$ is linear or branched $C_1$–$C_{18}$-alkylene or unsubstituted or $C_1$–$C_4$-alkyl- or $C_1$–$C_4$-alkoxy-substituted $C_6$–$C_{10}$-arylene, $C_7$–$C_{18}$-aralkylene, $C_6$–$C_{10}$-arylene-$C_1$–$C_2$-alkylene-$C_6$–$C_{10}$-arylene, $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene;

$A_2$ is $C_1$–$C_8$-alkylene; phenylene or benzylene;

m and n are each independently of the other the number 0 or 1;

X, $X_1$ and X' are each independently of the other a bivalent group —O— or —NR", wherein R" is hydrogen or $C_1$–$C_6$-alkyl;

(alk*) is $C_2$–$C_{12}$-alkylene;

and (oligomer) denotes (i) the radical of a telomer of formula

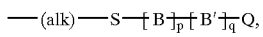     (8a)

wherein (alk) is $C_2$–$C_{12}$-alkylene,

Q is a monovalent group that is suitable to act as a polymerization chain-reaction terminator, p and q are each independently of another an integer from 0 to 350, wherein the total of (p+q) is an integer from 2 to 350, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (ii) the radical of an oligomer of the formula

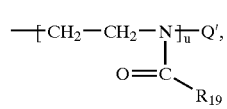     (8b)

wherein $R_{19}$ is hydrogen or unsubstituted or hydroxy-substituted $C_1$–$C_{12}$-alkyl, u is an integer from 2 to 250 and Q' is a radical of a polymerization initiator; or (iii) the radical of formula

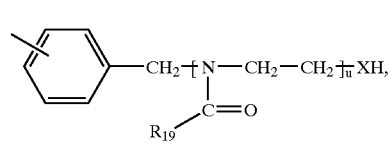     (8b')

wherein $R_{19}$, X and u are as defined above, or (iv) the radical of an oligomer of formula

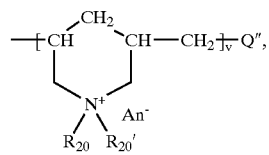     (8c)

wherein $R_{20}$ and $R_{20}'$ are each independently $C_1$–$C_4$-alkyl, An$^-$ is an anion, v is an integer from 2 to 250, and Q" is a monovalent group that is suitable to act as a polymerization chain-reaction terminator; or (v) the radical of an oligopeptide of formula —(CHR$_{21}$—C(O)—NH)$_t$—CHR$_{21}$—COOH      (8d) or —CHR$_{21}$—(NH—C(O)—CHR$_{21}$)$_t$—NH$_2$      (8d'), wherein $R_{21}$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—NH$_2$ and t is an integer from 2 to 250, or the radical of an oligopeptide based on proline or hydroxyproline; or (vi) the radical of a polyalkylene oxide of formula -(alk-O)$_z$—[CH$_2$—CH$_2$—O]$_r$—[CH$_2$—CH(CH$_3$)—O]$_s$—R$_{34}$(8e), wherein $R_{34}$ is hydrogen or $C_1$–$C_{24}$-alkyl, (alk) is $C_2$–$C_4$-alkylene, z is 0 or 1, r and s are each independently an integer from 0 to 250 and the total of (r+s) is from 2 to 250; or (vii) the radical of an oligosaccharide;

subject to the provisos that

A is not a direct bond if (oligomer) is a radical of formula (6a);

A is a radical of formula (7a), (7b) or (7d) or A and $R_{32}$, together with the adjacent double bond, are a radical of formula (7f) if (oligomer) is a radical of formula (8b), (8c), (8d) or (8e) or is the radical of an oligosaccharide;

A is a direct bond if (oligomer) is a radical of formula (8b'); and

A is a radical of formula (7c) or (7e) if (oligomer) is a radical of formula (8d').

18. A process according to claim 6, wherein a macromonomer of formula

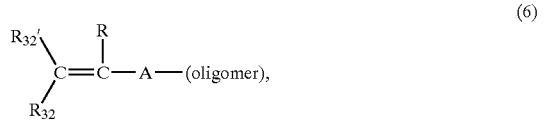
(6)

is applied in step (d), wherein $R_{32}$ is hydrogen, $C_1$–$C_6$-alkyl or a radical —COOR';

R, R' and $R_{32}'$ are each independently of the other hydrogen or $C_1$–$C_6$-alkyl;

A is a direct bond or is a radical of formula

—C(O)-(A$_1$)$_n$-X— (7a) or

-(A$_2$)$_m$—NH—C(O)—X— (7b); or

-(A$_2$)$_m$—X—C(O)— (7c); or

—C(O)—NH—C(O)—X— (7d); or

—C(O)—X$_1$-(alk*)-X—C(O)— (7e); or

A and $R_{32}$, together with the adjacent double bond, are a radical of formula

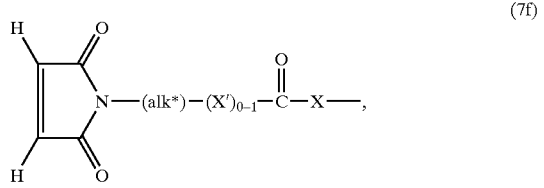
(7f)

$A_1$ is —O—$C_2$-$C_{12}$-alkylene which is unsubstituted or substituted by hydroxy, or is —O—$C_2$-$C_{12}$-alkylene-NH—C(O)— or —O—$C_2$-$C_{12}$-alkylene-O—C(O)—NH—$R_{33}$—NH—C(O)— or —NH-(Alk*)-C(O)—, wherein (Alk*) is $C_1$–$C_6$-alkylene and $R_{33}$ is linear or branched $C_1$–$C_{18}$-alkylene or unsubstituted or $C_1$–$C_4$-alkyl- or $C_1$–$C_4$-alkoxy-substituted $C_6$–$C_{10}$-arylene, $C_7$–$C_{18}$-aralkylene, $C_6$–$C_{10}$-arylene-$C_1$–$C_2$-alkylene-$C_6$–$C_{10}$-arylene, $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene;

$A_2$ is $C_1$–$C_8$-alkylene; phenylene or benzylene;

m and n are each independently of the other the number 0 or 1;

X, $X_1$ and X' are each independently of the other a bivalent group —O— or —NR'', wherein R'' is hydrogen or $C_1$–$C_6$-alkyl;

(alk*) is $C_2$–$C_{12}$-alkylene;

and (oligomer) denotes (i) the radical of a telomer of formula

(8a)

wherein (alk) is $C_2$–$C_{12}$-alkylene,

Q is a monovalent group that is suitable to act as a polymerization chain-reaction terminator, p and q are each independently of another an integer from 0 to 350, wherein the total of (p+q) is an integer from 2 to 350, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (ii) the radical of an oligomer of the formula

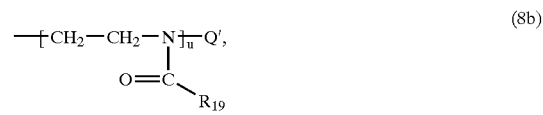
(8b)

wherein $R_{19}$ is hydrogen or unsubstituted or hydroxy-substituted $C_1$–$C_{12}$-alkyl, u is an integer from 2 to 250 and Q' is a radical of a polymerization initiator; or (iii) the radical of formula

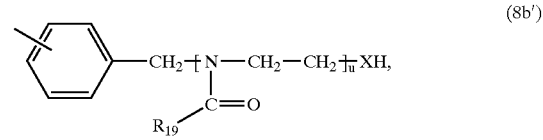
(8b')

wherein $R_{19}$, X and u are as defined above, or (iv) the radical of an oligomer of formula

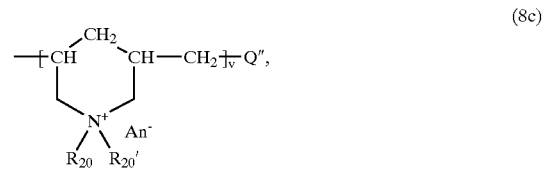
(8c)

wherein $R_{20}$ and $R_{20}'$ are each independently $C_1$–$C_4$-alkyl, An$^-$ is an anion, v is an integer from 2 to 250, and Q'' is a monovalent group that is suitable to act as a polymerization chain-reaction terminator; or (v) the radical of an oligopeptide of formula —(CHR$_{21}$—C(O)—NH)$_t$—CHR$_{21}$—COOH (8d) or —CHR$_{21}$—(NH—C(O)—CHR$_{21}$)$_t$—NH$_2$ (8d'), wherein $R_{21}$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—NH$_2$ and t is an integer from 2 to 250, or the radical of an oligopeptide based on proline or hydroxyproline; or (vi) the radical of a polyalkylene oxide of formula

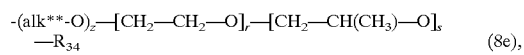
(8e), wherein $R_{34}$ is hydrogen or $C_1$–$C_{24}$-alkyl, (alk**) is $C_2$–$C_4$-alkylene, z is 0 or 1, r and s are each independently an integer from 0 to 250 and the total of (r+s) is from 2 to 250; or (vii) the radical of an oligosaccharide;

subject to the provisos that

A is not a direct bond if (oligomer) is a radical of formula (6a);

A is a radical of formula (7a), (7b) or (7d) or A and $R_{32}$, together with the adjacent double bond, are a radical of formula (7f) if (oligomer) is a radical of formula (8b), (8c), (8d) or (8e) or is the radical of an oligosaccharide;

A is a direct bond if (oligomer) is a radical of formula (8b'); and

A is a radical of formula (7c) or (7e) if (oligomer) is a radical of formula (8d').

19. A process according to claim 8, wherein (oligomer) is a radical of formula

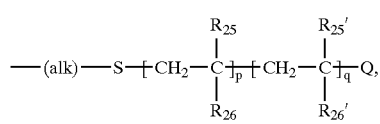
(8a')

wherein (alk) is $C_2$–$C_4$-alkylene, $R_{25}$ and $R_{25}'$ are each independently hydrogen or methyl, Q is a monovalent group that is suitable to act as a polymerization chain-reaction terminator, p and q are each independently an integer from 0 to 100 wherein the total of (p+q) is an integer from 5 to 100, and $R_{26}$ and $R_{26}'$ are each independently a radical —COOY, wherein Y is $C_1$–$C_2$-alkyl, $C_2$–$C_3$-alkyl, which is substituted by hydroxy, amino or N,N-di-$C_1$–$C_2$-alkylamino, or is a radical —$C_2$–$C_4$-alkylene-NH—C(O)—O-G wherein —O-G is the radical of trehalose; a radical —CO—$NY_1Y_2$, wherein $Y_1$ and $Y_2$ are each independently of the other hydrogen or $C_1$–$C_2$-alkyl which is unsubstituted or substituted by hydroxy, or $Y_1$ and $Y_2$ together with the adjacent N-atom form a N—$C_1$–$C_2$-alkylpiperazino or morpholino ring; a heterocyclic radical selected from the group consisting of N-pyrrolidonyl, 2- or 4-pyridinyl, 2-methylpyridin-5-yl, 2-, 3- oder 4-hydroxypyridinyl, N-ε-caprolactamyl, N-imidazolyl, 2-methylimidazol-1-yl, N-morpholinyl and 4-N-methylpiperazin-1-yl; —COOH; —$SO_3H$; o-, m- or p-sulfophenyl; o-, m- or p-sulfomethylphenyl; a radical —$CONY_6Y_6$ wherein $Y_6$ is $C_2$–$C_4$-alkyl substituted by sulfo, and $Y_8$ is hydrogen; $C_1$–$C_4$-alkyl which is substituted by —$NR_{23}R_{23}'R_{23}''{}^+An^-$ wherein $R_{23}$, $R_{23}'$ and $R_{23}''$ are each independently of another hydrogen or $C_1$–$C_4$-alkyl and $An^-$ is an anion; a radical —$C(O)OY_7$ wherein $Y_7$ is $C_2$–$C_4$-alkyl, which is substituted by —$NR_{23}R_{23}'R_{23}''{}^+An^-$ and is further unsubstituted or substituted by hydroxy, wherein $R_{23}$, $R_{23}'$, $R_{23}''$ and $^+An^-$ are as defined; and a radical —C(O)O—$CH_2$—CH($OY_8$)—$CH_2$—O—$PO_2^-$—$(CH_2)_2$—$N(CH_3)_3^+$, wherein $Y_8$ is hydrogen or acyl radical of a higher fatty acid.

20. A process according to claim 6, wherein in step (d) a macromonomer of formula

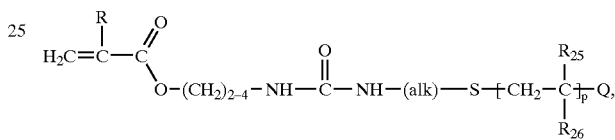
(6b)

is applied, wherein R is hydrogen or methyl, (alk) is $C_2$–$C_4$-alkylene, $R_{25}$ is hydrogen or methyl, p is an integer of 5 to 50, Q is a monovalent group that is suitable to act as a polymerization chain-reaction terminator, and $R_{26}$ is a radical —$CONH_2$, —$CON(CH_3)_2$ or

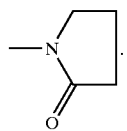

* * * * *